(12) United States Patent
Ushida et al.

(10) Patent No.: US 8,765,706 B2
(45) Date of Patent: Jul. 1, 2014

(54) COMPOSITION COMPRISING RNA DERIVED FROM LACTIC ACID BACTERIUM AS EFFECTIVE COMPONENT

(75) Inventors: Kazunari Ushida, Kyoto (JP); Ryo Inoue, Kyoto (JP); Takumi Watanabe, Saitama (JP)

(73) Assignees: Kyoto Prefectural Public University Corporation, Kyoto (JP); Combi Corporation, Tokyo (JP)

( * ) Notice: Subject to any disclaimer, the term of this patent is extended or adjusted under 35 U.S.C. 154(b) by 0 days.

(21) Appl. No.: 13/393,060

(22) PCT Filed: Sep. 2, 2010

(86) PCT No.: PCT/JP2010/065051
§ 371 (c)(1),
(2), (4) Date: May 9, 2012

(87) PCT Pub. No.: WO2011/027829
PCT Pub. Date: Mar. 10, 2011

(65) Prior Publication Data
US 2012/0220760 A1 Aug. 30, 2012

(30) Foreign Application Priority Data
Sep. 2, 2009 (JP) .................................. 2009-202845

(51) Int. Cl.
*A61K 48/00* (2006.01)
(52) U.S. Cl.
USPC .......................................................... 514/44
(58) Field of Classification Search
None
See application file for complete search history.

(56) References Cited

U.S. PATENT DOCUMENTS 6,503,512 B1  1/2003  Torossian

FOREIGN PATENT DOCUMENTS

| JP | A-08-500846 | 1/1996 |
|----|----|----|
| JP | A-2004-502633 | 1/2004 |
| JP | A-2006-083184 | 3/2006 |
| JP | A-2006-223110 | 8/2006 |
| JP | A-2009-102292 | 5/2009 |
| WO | WO 2005/087241 A1 | 9/2005 |
| WO | WO 2009/005123 A1 | 1/2009 |
| WO | WO 2009/005124 A1 | 1/2009 |

OTHER PUBLICATIONS

Terada et al., "Effects of the Consumption of Heat-Killed *Enterococcus faecalis* EC-12 Preparation on Microbiota and Metabolic Activity of the Faeces in Healthy Adults," *Microbial Ecology in Health and Disease*, 2004, pp. 188-194, vol. 16, Taylor & Francis.
Takahashi et al., "Antitumor Effects of the Intravesical Instillation of Heat Killed Cells of the *Lactobacillus casei* Strain Shirota on the Murine Orthotopic Bladder Tumor MBT-2," *The Journal of Urology*, 2001, pp. 2506-2511, vol. 166, American Urological Association, Inc.
Shida, "Allergy Suppression Effect of Lactic Acid Bacterium, Particularly of *Lactobacillus casei* strain Shirota," *Food Industry*, 2002, pp. 49-54, Japan (with translation).
Kuramoto et al., "The Effect of the Heat-Killed Lactococci, EC-12 on Host Defence Mechanism in Mice After Infection with *Listeria monocytogenes*," *Journal of New Remedies & Clinics*, 2004, pp. 298-300, vol. 53, No. 3, Japan.
Ishikawa et al., "Lipid Metablolish Improvement Function of Fermented Milk Containing *Lactobacillus casei* strain Shirota," *Food Industry*, 2001, pp. 26-33, Japan (with translation).
Matsuguchi et al., "Lipoteichoic Acids from *Lactobacillus* Strains Elicit Strong Tumor Necrosis Factor Alpha-Inducing Activities in Macrophages through Toll-Like Receptor 2," *Clinical and Diagnostic Laboratory Immunology*, 2003, pp. 259-266, vol. 10, No. 2, American Society for Microbiology.
Oct. 19, 2010 International Search Report issued in International Patent Application No. PCT/JP2010/065051 (with translation).
Mar. 29, 2012 International Preliminary Report on Patentability issued in International Patent Application No. PCT/JP2010/065051.

*Primary Examiner* — Brian J Gangle
(74) *Attorney, Agent, or Firm* — Oliff PLC

(57) ABSTRACT

A composition has an immunomodulation action, and comprises an RNA derived from a lactic acid bacterium as an effective component. Alternatively, a composition has a cytokine production-modulating action, and includes an RNA derived from a lactic acid bacterium as an effective component.

9 Claims, 18 Drawing Sheets

SEQUENCE LISTING

```
<160> NUMBER OF SEQ ID NOS: 205

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 1
tgaactggcg ttggaagc                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 2
gcgggtctgg tttgatga                                                 18

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 3
tgtccgtcgt ggatctgac                                                19

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 4
cctgcttcac caccttcttg                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct-Immunoregulatory DNA
```

-continued

```
                sequence

<400> SEQUENCE: 5
tgcttgcaag cttgcaagca                                                   20

<210> SEQ ID NO 6
<211> LENGTH: 15
<212> TYPE: DNA
<213> ORGANISM: Artificial Sequence
<220> FEATURE:
<223> OTHER INFORMATION: Synthetic Construct-Immunoregulatory DNA
        sequence

<400> SEQUENCE: 6
tcctggaggg gttgt                                                        15

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct-Immunostimulatory DNA
        sequence

<400> SEQUENCE: 7
tgactgtgaa cgttcgagat ga                                                22

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 8
cccctgaagt ttatccagtg tta                                               23

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 9
gcagctttct ctacctttgt tca                                               23

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 10
gaagaaagag cttcccctga a                                                 21

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 11
cgcagctttc tctacctttg tt                                                22
```

```
<210> SEQ ID NO 12
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 12
catccacgtg ttggctca                                                 18

<210> SEQ ID NO 13
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 13
gatcatcttg ctggtgaatg agt                                           23

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 14
tgcccttgct gttcttctct                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 15
gtggaatctt ccggctgtag                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 16
gccctctctc tcctcttgct                                               20

<210> SEQ ID NO 17
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 17
gagggtcaga gcccattg                                                 18

<210> SEQ ID NO 18
<211> LENGTH: 21
<212> TYPE: DNA
<213> ORGANISM: Artificial Sequence
<220> FEATURE:
```

```
<223> OTHER INFORMATION: Synthetic Construct-primer sequence

<400> SEQUENCE: 18
tgcagaggac tctgagacag c                                         21

<210> SEQ ID NO 19
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 19
gagtggtgtc cgagccata                                            19

<210> SEQ ID NO 20
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 20
ccttgtggct gtccttgg                                             18

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 21
gcgacgatct tcttttcca                                            20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 22
ttctgtgcct gctgctcata                                           20

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 23
ttgacatagc agcatgtgga t                                         21

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 24
ttctttgcct gctgctcata                                           20
```

-continued

```
<210> SEQ ID NO 25
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 25
gcaggtgact ggagccttat                                                 20

<210> SEQ ID NO 26
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 26
tgggcccaga tcacacat                                                   18

<210> SEQ ID NO 27
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 27
cccatgtgaa acatttcaat ttc                                             23

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 28
cacggtcact tccttcacct                                                 20

<210> SEQ ID NO 29
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 29
tggggatctt cttactggtc a                                               21

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 30
ccatcagtcc tcaggtattg g                                               21

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct-primer sequence
```

<400> SEQUENCE: 31
cttccggacg tgaatcttct                                                20

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 32
tgcttctggg gactttttctg                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 33
gaatggcccc tttgaagtaa                                                20

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 34
tgtggcctgc ctcagattat                                                20

<210> SEQ ID NO 35
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 35
agtcttccgc atcattagca c                                              21

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 36
aactgggtga aagggctgt                                                 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 37
gtccaattcc atcccaaaaa                                                20

<210> SEQ ID NO 38
<211> LENGTH: 18

```
<212> TYPE: DNA
<213> ORGANISM: Artificial Sequence
<220> FEATURE:
<223> OTHER INFORMATION: Synthetic Construct-primer sequence

<400> SEQUENCE: 38
tccaagggct gcaagaga                                                 18

<210> SEQ ID NO 39
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 39
tgaagttcgt gggggatct                                                19

<210> SEQ ID NO 40
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 40
tcttgctgtg gcaattcaga                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 41
gagggtgacg gatgtagtcc                                               20

<210> SEQ ID NO 42
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 42
gcagcatctg tcccaagg                                                 18

<210> SEQ ID NO 43
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 43
gcagcttggg gtcagtaca                                                19

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 44
```

```
gagtgccacc ctaggtcatc                                          20

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 45
ccagctggtg cttactctga                                          20

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct-primer sequencee

<400> SEQUENCE: 46
gcaccagtga cggtgtgata                                          20

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 47
tgaatctctg cacccatttg                                          20

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 48
cagtgtccag cttggtgttg                                          20

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 49
tgaaattagg gcagcaggac                                          20

<210> SEQ ID NO 50
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 50
acagccactc ccaagcag                                            18

<210> SEQ ID NO 51
<211> LENGTH: 18
<212> TYPE: DNA
<213> ORGANISM: Artificial Sequence
```

```
<220> FEATURE:
<223> OTHER INFORMATION: Synthetic Construct-primer sequence

<400> SEQUENCE: 51
aggtgacagt ccccatcg                                                    18

<210> SEQ ID NO 52
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 52
gttcttcatc ctgtggtgct c                                                21

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 53
agggaagact ccacattcca                                                  20

<210> SEQ ID NO 54
<211> LENGTH: 26
<212> TYPE: DNA
<213> ORGANISM: Artificial Sequence
<220> FEATURE:
<223> OTHER INFORMATION: Synthetic Construct-primer sequence

<400> SEQUENCE: 54
ataatgggct tttacattct ttaacc                                           26

<210> SEQ ID NO 55
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 55
agtcctttga acgtctctgt cc                                               22

<210> SEQ ID NO 56
<211> LENGTH: 26
<212> TYPE: DNA
<213> ORGANISM: Artificial Sequence
<220> FEATURE:
<223> OTHER INFORMATION: Synthetic Construct-primer sequence

<400> SEQUENCE: 56
aaaatcatcc aaaagatact gaacaa                                           26

<210> SEQ ID NO 57
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 57
ctttggttct tccgttgagg                                                  20
```

-continued

<210> SEQ ID NO 58
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 58
ccccaggctt cagataatca                                              20

<210> SEQ ID NO 59
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 59
tctgatttag aatgcaggtc ctt                                          23

<210> SEQ ID NO 60
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 60
tgggatccat cttaagcaca                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 61
ccattcttca gggtggctat                                              20

<210> SEQ ID NO 62
<211> LENGTH: 24
<212> TYPE: DNA
<213> ORGANISM: Artificial Sequence
<220> FEATURE:
<223> OTHER INFORMATION: Synthetic Construct-primer sequence

<400> SEQUENCE: 62
gggtgtgtta agagtgttct tacg                                         24

<210> SEQ ID NO 63
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 63
acacagcagc tttctaaaac cat                                          23

<210> SEQ ID NO 64
<211> LENGTH: 20
<212> TYPE: DNA
<213> ORGANISM: Artificial Sequence
<220> FEATURE:
<223> OTHER INFORMATION: Synthetic Construct-primer sequence -continued

```
<400> SEQUENCE: 64
gcccacttca taacctccag                                                   20

<210> SEQ ID NO 65
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 65
atgggtccat gccatcag                                                     18

<210> SEQ ID NO 66
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 66
cttttcctct tgggcatcat                                                   20

<210> SEQ ID NO 67
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 67
gcatcgtgca ttccttatca                                                   20

<210> SEQ ID NO 68
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 68
gctgccgtca ttttctgc                                                     18

<210> SEQ ID NO 69
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 69
tctcactggc ccgtcatc                                                     18

<210> SEQ ID NO 70
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 70
gctgctgaga tgaacaggaa                                                   20

<210> SEQ ID NO 71
```

```
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 71
ccctgtttga acataaggaa gc                                              22

<210> SEQ ID NO 72
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 72
ctgtgccctt cagattgttg                                                 20

<210> SEQ ID NO 73
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 73
taatttcggg tcaatgcaca                                                 20

<210> SEQ ID NO 74
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 74
catagatcgg attcaagtta cgc                                             23

<210> SEQ ID NO 75
<211> LENGTH: 27
<212> TYPE: DNA
<213> ORGANISM: Artificial Sequence
<220> FEATURE:
<223> OTHER INFORMATION: Synthetic Construct-primer sequence

<400> SEQUENCE: 75
cacacatata actttcttca tcttggt                                         27

<210> SEQ ID NO 76
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 76
ttgagaccgt tcacagcact                                                 20

<210> SEQ ID NO 77
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 77
```
ctctctgagc ggaagctttg                                            20

<210> SEQ ID NO 78
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 78
tgctcaaggc tggtccat                                              18

<210> SEQ ID NO 79
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 79
gacatcgtag ctcttgagtg tca                                        23

<210> SEQ ID NO 80
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 80
tgaactagtg gactgctttg agc                                        23

<210> SEQ ID NO 81
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 81
gcaaatgttt ttggtggtga                                            20

<210> SEQ ID NO 82
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 82
gacttctcct cctgactttc ctg                                        23

<210> SEQ ID NO 83
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 83
ggacttcagt ccccacacc                                             19

<210> SEQ ID NO 84
<211> LENGTH: 20
<212> TYPE: DNA

```
<213> ORGANISM: Artificial Sequence
<220> FEATURE:
<223> OTHER INFORMATION: Synthetic Construct-primer sequence

<400> SEQUENCE: 84
cgcgttcttc catttgtgta                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 85
catgatttcg catttcgtca                                              20

<210> SEQ ID NO 86
<211> LENGTH: 24
<212> TYPE: DNA
<213> ORGANISM: Artificial Sequence
<220> FEATURE:
<223> OTHER INFORMATION: Synthetic Construct-primer sequence

<400> SEQUENCE: 86
tggacaaaat actctggaaa caca                                         24

<210> SEQ ID NO 87
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 87
tgtgaaatct gaaatctcca tcc                                          23

<210> SEQ ID NO 88
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 88
acctgtaaat gccatgcaag t                                            21

<210> SEQ ID NO 89
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 89
tgtcttccat ttcctttgat ttg                                          23

<210> SEQ ID NO 90
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 90
gagcatcaac aacacgttcc                                              20
```

```
<210> SEQ ID NO 91
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 91
tgaaagtgtg atcttgggac a                                             21

<210> SEQ ID NO 92
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 92
ctcaggatca ctttcagaag agc                                           23

<210> SEQ ID NO 93
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 93
ggcattcatc tttggaatcg                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 94
gagacatccg ttcccectac                                               20

<210> SEQ ID NO 95
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 95
gtcggaactg acccttgaaa                                               20

<210> SEQ ID NO 96
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 96
tggttcgcca ctctaatcag t                                             21

<210> SEQ ID NO 97
<211> LENGTH: 22
<212> TYPE: DNA
<213> ORGANISM: Artificial Sequence
<220> FEATURE:
```

<223> OTHER INFORMATION: Synthetic Construct-primer sequence

<400> SEQUENCE: 97
tctggtgtag aaagggaagt gg                                              22

<210> SEQ ID NO 98
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 98
cagggaaacc caggaaaaac                                                 20

<210> SEQ ID NO 99
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 99
atcttggcag aagcacacct                                                 20

<210> SEQ ID NO 100
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 100
agaagaaagg ctcgctcaga                                                 20

<210> SEQ ID NO 101
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 101
ggctccatcg tgtaatccat                                                 20

<210> SEQ ID NO 102
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 102
tctggcacag aagctgattg                                                 20

<210> SEQ ID NO 103
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 103
catgccagga ataaggcttg                                                 20

-continued

```
<210> SEQ ID NO 104
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 104
accaagccca cagagcag                                                 18

<210> SEQ ID NO 105
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 105
gccaccatca gggagaca                                                 18

<210> SEQ ID NO 106
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 106
ttctgagctt gctgggaaac                                               20

<210> SEQ ID NO 107
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 107
gggtccttcg cctgtataag a                                             21

<210> SEQ ID NO 108
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 108
caggaatggg agtaggtgga                                               20

<210> SEQ ID NO 109
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 109
tttcctagtt tcccctccaa at                                            22

<210> SEQ ID NO 110
<211> LENGTH: 18
<212> TYPE: DNA
<213> ORGANISM: Artificial Sequence
<220> FEATURE:
<223> OTHER INFORMATION: Synthetic Construct-primer sequence
```

<400> SEQUENCE: 110
aggcagcacg agacctga 18

<210> SEQ ID NO 111
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 111
ggcatctagc acttgacgtt c 21

<210> SEQ ID NO 112
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 112
tggaaccgat cagtgtgagt 20

<210> SEQ ID NO 113
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 113
gggcaggaag atcctattga 20

<210> SEQ ID NO 114
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 114
tttctgctcc cagcatcc 18

<210> SEQ ID NO 115
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 115
ttttatttct gtgcccggtt t 21

<210> SEQ ID NO 116
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 116
agctactggg cttctcttct ga 22

<210> SEQ ID NO 117
<211> LENGTH: 20

```
<212> TYPE: DNA
<213> ORGANISM: Artificial Sequence
<220> FEATURE:
<223> OTHER INFORMATION: Synthetic Construct-primer sequence

<400> SEQUENCE: 117
tcgtagtgcc catcgtacag                                           20

<210> SEQ ID NO 118
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 118
acatgatacc catggggaag t                                         21

<210> SEQ ID NO 119
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 119
gtgcacgaag tgttgctttg                                           20

<210> SEQ ID NO 120
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 120
aagttccctt cccatctgct                                           20

<210> SEQ ID NO 121
<211> LENGTH: 25
<212> TYPE: DNA
<213> ORGANISM: Artificial Sequence
<220> FEATURE:
<223> OTHER INFORMATION: Synthetic Construct-primer sequence

<400> SEQUENCE: 121
caaaattctc tagatccagt tcagg                                     25

<210> SEQ ID NO 122
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 122
tcttgctggc acccattc                                             18

<210> SEQ ID NO 123
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 123
```
catgagagtt ttgagcttgt gg                                      22

<210> SEQ ID NO 124
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 124
ggggcttcac ttctctgctt                                         20

<210> SEQ ID NO 125
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 125
agcatcctct gagatttgac g                                       21

<210> SEQ ID NO 126
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 126
gatacaggga ttgcacccat a                                       21

<210> SEQ ID NO 127
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 127
tcccccaaag gagtacatta ga                                      22

<210> SEQ ID NO 128
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 128
ggactctgat catggcactg                                         20

<210> SEQ ID NO 129
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 129
ctgatccatg cattggtagg t                                       21

<210> SEQ ID NO 130
<211> LENGTH: 18
<212> TYPE: DNA
<213> ORGANISM: Artificial Sequence -continued

```
<220> FEATURE:
<223> OTHER INFORMATION: Synthetic Construct-primer sequence

<400> SEQUENCE: 130
ctggagccga gtgaggtc                                                 18

<210> SEQ ID NO 131
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 131
cggcaagcat tgttctcc                                                 18

<210> SEQ ID NO 132
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 132
tcatggatgg atgctgagtt                                               20

<210> SEQ ID NO 133
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 133
tggccatgaa gatcacacc                                                19

<210> SEQ ID NO 134
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 134
ggtaccgtca gtgctggaa                                                19

<210> SEQ ID NO 135
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 135
gggttttctg tcttggctca                                               20

<210> SEQ ID NO 136
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 136
gatcctggcc tatctctgac tc                                            22
```

```
<210> SEQ ID NO 137
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 137
cgtgtccaca tcgaaaacac                                              20

<210> SEQ ID NO 138
<211> LENGTH: 24
<212> TYPE: DNA
<213> ORGANISM: Artificial Sequence
<220> FEATURE:
<223> OTHER INFORMATION: Synthetic Construct-primer sequence

<400> SEQUENCE: 138
caaacgtttt accttccttt gtct                                         24

<210> SEQ ID NO 139
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 139
atggaagatg gcactggttc                                              20

<210> SEQ ID NO 140
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 140
gaatcctcca tctcccaaca t                                            21

<210> SEQ ID NO 141
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 141
ccagagtctc agccagcact                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 142
tcaagccatc cttgtgctaa                                              20

<210> SEQ ID NO 143
<211> LENGTH: 24
<212> TYPE: DNA
<213> ORGANISM: Artificial Sequence
<220> FEATURE:
<223> OTHER INFORMATION: Synthetic Construct-primer sequence
```

<400> SEQUENCE: 143
gtcttttgat gtgaagaggt tcaa                                              24

<210> SEQ ID NO 144
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 144
ctggcttcca tcatgaacaa                                                   20

<210> SEQ ID NO 145
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 145
agagggctgt ggtggagaa                                                    19

<210> SEQ ID NO 146
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 146
cacagccctc tccatcaact a                                                 21

<210> SEQ ID NO 147
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 147
catttccgaa tgttcgtcct                                                   20

<210> SEQ ID NO 148
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 148
atctggagga actggcaaaa                                                   20

<210> SEQ ID NO 149
<211> LENGTH: 24
<212> TYPE: DNA
<213> ORGANISM: Artificial Sequence
<220> FEATURE:
<223> OTHER INFORMATION: Synthetic Construct-primer sequence

<400> SEQUENCE: 149
ttcaagactt caaagagtct gagg                                              24

<210> SEQ ID NO 150

```
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 150
tcttctcatt cctgcttgtg g                                      21

<210> SEQ ID NO 151
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 151
ggtctgggcc atagaactga                                        20

<210> SEQ ID NO 152
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 152
tggagcaaca tgtggaactc                                        20

<210> SEQ ID NO 153
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 153
cagcagccgg ttaccaag                                          18

<210> SEQ ID NO 154
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 154
ttggttaaat gacctgcaac a                                      21

<210> SEQ ID NO 155
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 155
gagcgctcac gaacagttg                                         19

<210> SEQ ID NO 156
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 156
```

-continued tgtaatgaaa gacggcacac c          21

<210> SEQ ID NO 157
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 157
tcttctttgg gtattgcttg g          21

<210> SEQ ID NO 158
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 158
gctgttgatg gacctacagg a          21

<210> SEQ ID NO 159
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 159
ttcaattctg tggcctgctt          20

<210> SEQ ID NO 160
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 160
tacatctgcg aatgactctg c          21

<210> SEQ ID NO 161
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 161
ggctgaggtg gtctagaggt t          21

<210> SEQ ID NO 162
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 162
gagagatcat cggcatttg a          21

<210> SEQ ID NO 163
<211> LENGTH: 20
<212> TYPE: DNA

```
<213> ORGANISM: Artificial Sequence
<220> FEATURE:
<223> OTHER INFORMATION: Synthetic Construct-primer sequence

<400> SEQUENCE: 163
tctgtggtgt tcttcgttgc                                                  20

<210> SEQ ID NO 164
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 164
acattgaccg ccaaaaagag                                                  20

<210> SEQ ID NO 165
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 165
atccaggaac tgcctcgtc                                                   19

<210> SEQ ID NO 166
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 166
gatggatgct accaaactgg a                                                21

<210> SEQ ID NO 167
<211> LENGTH: 24
<212> TYPE: DNA
<213> ORGANISM: Artificial Sequence
<220> FEATURE:
<223> OTHER INFORMATION: Synthetic Construct-primer sequence

<400> SEQUENCE: 167
ccaggtagct atggtactcc agaa                                             24

<210> SEQ ID NO 168
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 168
cgcagaccat gttccatgt                                                   19

<210> SEQ ID NO 169
<211> LENGTH: 24
<212> TYPE: DNA
<213> ORGANISM: Artificial Sequence
<220> FEATURE:
<223> OTHER INFORMATION: Synthetic Construct-primer sequence

<400> SEQUENCE: 169
tctttaatgt ggcactcaga tgat                                             24
```

```
<210> SEQ ID NO 170
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 170
cagagccaca tgctcctaga                                              20

<210> SEQ ID NO 171
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 171
tgtccagctg gtcctttgtt                                              20

<210> SEQ ID NO 172
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 172
cctctgaccc ttaaggagct tat                                          23

<210> SEQ ID NO 173
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 173
cgttgcacag gggagtct                                                18

<210> SEQ ID NO 174
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 174
tgtgaaggtc aacctcaaag tc                                           22

<210> SEQ ID NO 175
<211> LENGTH: 25
<212> TYPE: DNA
<213> ORGANISM: Artificial Sequence
<220> FEATURE:
<223> OTHER INFORMATION: Synthetic Construct-primer sequence

<400> SEQUENCE: 175
agggatatct atcagggtct tcatt                                        25

<210> SEQ ID NO 176
<211> LENGTH: 27
<212> TYPE: DNA
<213> ORGANISM: Artificial Sequence
<220> FEATURE:
```

```
<223> OTHER INFORMATION: Synthetic Construct-primer sequence

<400> SEQUENCE: 176
catgtacaaa gacagtgaag taagagg                                               27

<210> SEQ ID NO 177
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 177
tttcaggtgg atccatttcc                                                       20

<210> SEQ ID NO 178
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 178
ggtggtatct cgggaaggac                                                       20

<210> SEQ ID NO 179
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 179
ccccttgatg taaatgaaag aca                                                   23

<210> SEQ ID NO 180
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 180
aacagacgcg ctttccag                                                         18

<210> SEQ ID NO 181
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 181
aggaggagct gagaggtcta cat                                                   23

<210> SEQ ID NO 182
<211> LENGTH: 23
<212> TYPE: DNA
<213> ORGANISM: Artificial Sequence
<220> FEATURE:
<223> OTHER INFORMATION: Synthetic Construct-primer sequence

<400> SEQUENCE: 182
ttcgtctttc acaagtgtct tca                                                   23
```

```
<210> SEQ ID NO 183
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 183
tgccagtaga ttcggtcttc a                                              21

<210> SEQ ID NO 184
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 184
gaagccgaat cagcctagc                                                 19

<210> SEQ ID NO 185
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 185
cagcgttact atcccgctct                                                20

<210> SEQ ID NO 186
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 186
cagcttgtct cctgaaaatc g                                              21

<210> SEQ ID NO 187
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 187
aaatgttttg tcggggagtg                                                20

<210> SEQ ID NO 188
<211> LENGTH: 18
<212> TYPE: DNA
<213> ORGANISM: Artificial Sequence
<220> FEATURE:
<223> OTHER INFORMATION: Synthetic Construct-primer sequence

<400> SEQUENCE: 188
cttgctctgg ggatcctg                                                  18

<210> SEQ ID NO 189
<211> LENGTH: 20
<212> TYPE: DNA
<213> ORGANISM: Artificial Sequence
<220> FEATURE:
<223> OTHER INFORMATION: Synthetic Construct-primer sequence
```

<400> SEQUENCE: 189
ggctccgatt ttgatagcat                                           20

<210> SEQ ID NO 190
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 190
tgtggagtca ccgcaaaac                                            19

<210> SEQ ID NO 191
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 191
tcctctgtgc ctggaactct                                           20

<210> SEQ ID NO 192
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 192
caaaccagac ctgcgaaca                                            19

<210> SEQ ID NO 193
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 193
tgtcttccca caaggctctc                                           20

<210> SEQ ID NO 194
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 194
ctgctgcctc tccatctgta                                           20

<210> SEQ ID NO 195
<211> LENGTH: 25
<212> TYPE: DNA
<213> ORGANISM: Artificial Sequence
<220> FEATURE:
<223> OTHER INFORMATION: Synthetic Construct-primer sequence

<400> SEQUENCE: 195
aaaaatgaga acagttgatg aatcc                                     25

<210> SEQ ID NO 196
<211> LENGTH: 20

```
<212> TYPE: DNA
<213> ORGANISM: Artificial Sequence
<220> FEATURE:
<223> OTHER INFORMATION: Synthetic Construct-primer sequence

<400> SEQUENCE: 196
gggcaggtga ccaatctgta                                              20

<210> SEQ ID NO 197
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 197
ataggacgac ggtggagga                                               19

<210> SEQ ID NO 198
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 198
tcctcctcag accgctttt                                               19

<210> SEQ ID NO 199
<211> LENGTH: 21
<212> TYPE: DNA
<213> ORGANISM: Artificial Sequence
<220> FEATURE:
<223> OTHER INFORMATION: Synthetic Construct-primer sequence

<400> SEQUENCE: 199
cctggttcat catcgctaat c                                            21

<210> SEQ ID NO 200
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 200
ctaaggccaa ccgtgaaaag                                              20

<210> SEQ ID NO 201
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 201
accagaggca tacagggaca                                              20

<210> SEQ ID NO 202
<211> LENGTH: 20
<212> TYPE: DNA
<213> ORGANISM: Artificial Sequence
<220> FEATURE:
<223> OTHER INFORMATION: Synthetic Construct-primer sequence

<400> SEQUENCE: 202
```

```
agtaaccgag gcctgtcctt                                                    20

<210> SEQ ID NO 203
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 203
gtcactcggc aactcagga                                                     19

<210> SEQ ID NO 204
<211> LENGTH: 19
<212> TYPE: DNA
<213> ORGANISM: Artificial Sequence
<220> FEATURE:
<223> OTHER INFORMATION: Synthetic Construct-primer sequence

<400> SEQUENCE: 204
gactccaggg gacaggcta                                                     19

<210> SEQ ID NO 205
<211> LENGTH: 22
<212> TYPE: DNA
<213> ORGANISM: Artificial Sequence
<220> FEATURE:
<223> OTHER INFORMATION: Synthetic Construct-primer sequence

<400> SEQUENCE: 205
ggagatggtt agcttctgag ga                                                 22
```

COMPOSITION COMPRISING RNA DERIVED FROM LACTIC ACID BACTERIUM AS EFFECTIVE COMPONENT

TECHNICAL FIELD

The present invention relates to a composition comprising an RNA derived from a lactic acid bacterium as an effective component, and to use of the composition for immunomodulation or for cytokine production modulation.

BACKGROUND ART

Macrophages and dendritic cells which are cells taking charge of the innate immunity express receptors (pattern-recognition receptors: PRRs) for recognizing specific molecular patterns (pathogen-associated molecular patterns: PAMPs) present on pathogenic microbes invading an organism.

One of PRRs playing the most important role for macrophages and dendritic cells to recognize foreign microbes is a Toll-like receptor (TLR). At present, 13 types of TLRs have been identified in mammals. It is known that most of these TLRs mainly recognize PAMPs of bacteria. After a TLR recognizes PAMPs, TIR (Toll/IL-1 receptor) in a cytoplasm sends a signal, and finally activation of NF-κB and MAPK (mitogen-activated protein kinase) is induced.

In macrophages and dendritic cells, the activation of NF-κB, MAPK, and the like induces production of inflammatory cytokines such as TNF-α (tumor necrosis factor-α), IL (interleukin)-6, and IL-12, and is involved in suppression of infection expansion and determination of differentiation for T cells. Moreover, a dendritic cell matured by TLR signaling presents the antigen to a lymphocyte such as a B cell and a T cell, and induces proliferation of the antigen-specific lymphocyte. In this manner, TLRs play an important role not only in the innate immune system but also in the adaptive immune system.

Recently, immunostimulatory substances have been developed utilizing TLR signaling. For example, Patent Literature 1 discloses a technique for the purpose of immunostimulation by TLR signaling: an immunostimulatory composition comprising an isolated RNA oligomer 5 to 40 nucleotides long having a base sequence comprising at least one guanine and at least one uracil, and optionally a cationic lipid. Moreover, it is described that an isolated RNA oligomer produced by a nucleic acid synthesis method is preferably used as a nucleic acid serving as an effective component of the immunostimulatory composition (Paragraph 73 in the specification). Nevertheless, the literature does not disclose a result of an experiment conducted in a living organism, a so-called in vivo experiment. Accordingly, it is not certain whether such a synthetic RNA oligomer actually demonstrates a safe immunostimulating action in a living organism. In addition, the literature does not specifically disclose at all to what degree such a synthetic RNA oligomer demonstrates an effective immunostimulating effect in a living organism.

Further, Patent Literature 2 discloses a technique: an oligodeoxynucleotide having an immunostimulating action, and comprising a certain specific base sequence. Nevertheless, Patent Literature 2 merely discloses the result of examining a mitogen activity, in other words, cell division promoting activity, in the genomic DNA of a bacterium belonging to the genus *Bifidobacterium* in Example, and does not disclose at all a direct experimental result for whether an immunostimulating action exists or not.

Meanwhile, studies have reported so far that the health effects of lactic acid bacteria include actions for intestinal function regulation, cancer risk reduction, prevention of atopic dermatitis, allergy reduction, biological defense mechanism, blood cholesterol reduction, blood pressure reduction, and so forth (Non Patent Literatures 1 to 5). Moreover, lactic acid bacteria taken orally are incorporated in the intestinal tract from the Peyer's patch (PP) and phagocytized by macrophages, dendritic cells, and the like located in the PP. This is believed to activate the immune cells, stimulating innate immunity. Furthermore, it has been reported that lactic acid bacteria are recognized by TLR (Non Patent Literature 6). It is believed that lactic acid bacteria modulate the function of macrophages and dendritic cells through TLR signaling. Thus, identification of the effective component of lactic acid bacteria leads to development of drugs for modulating specific cytokine production, and can be utilized in the medical field, as well. Nevertheless, the detail of the substance which may serve as the main source of an immunomodulation action and a cytokine production-modulating-action of lactic acid bacteria has not been revealed yet.

CITATION LIST

Patent Literatures

[PTL 1] Japanese Unexamined Patent Application Publication No. 2006-83184
[PTL 2] Japanese Unexamined Patent Application Publication No. 2006-223110

Non Patent Literatures

[NPL 1] Microbial Ecology in Health and Disease, 2004, vol. 16, pp. 188-194
[NPL 2] The Journal of Urology, 2001, vol. 166, pp. 2506-2511
[NPL 3] Food Industry, 2002, vol. 45, no. 14, pp. 49-54
[NPL 4] Journal of New Remedies & Clinics, 2004, vol. 53, no. 3, pp. 298-308
[NPL 5] Food Industry, 2001, vol. 44, no. 4, pp. 26-33
[NPL 6] Clinical and Diagnostic Laboratory Immunology, March 2003, vol. 10, no. 2, pp. 259-266

SUMMARY OF INVENTION

Technical Problem

The present invention has been made in view of the above-described circumstances. An object of the present invention is to provide a composition having an immunomodulation action and a composition having a cytokine production-modulating action by utilizing a substance identified from a lactic acid bacterium as a main source of the immunomodulation action and the cytokine production-modulating action.

Solution to Problem

The present Inventors have earnestly studied in order to achieve the above object. As a result, it has been found out that an RNA derived from a lactic acid bacterium promotes production of IL-12 and the like, or suppresses production of TNF-α, which are mediated by TLR7, Myd88, and the like. This discovery has led to the completion of the present invention.

More specifically, the present invention provides the following inventions.

(1) A composition having an immunomodulation action, and comprising an RNA derived from a lactic acid bacterium as an effective component.
(2) A composition having a cytokine production-modulating action, and comprising an RNA derived from a lactic acid bacterium as an effective component.
(3) The composition according to (2), which has an action of promoting production of at least one cytokine selected from the group consisting of IL-12, CCL2, CCL5, CCL7, CXCL10, IL-6, and IL-1α.
(4) The composition according to (3), wherein
the IL-12 is IL-12p40.
(5) The composition according to (2), which has an action of suppressing TNF-α production.
(6) The composition according to any one of (1) to (5), which has any one of the immunomodulation action and the cytokine production-modulating action dependently on at least one biomolecule selected from the group consisting of TLR7 and Myd88.
(7) The composition according to any one of (1) to (6), wherein
the RNA is a single-stranded RNA.
(8) The composition according to any one of (1) to (7), wherein
the lactic acid bacterium is at least one lactic acid bacterium selected from the group consisting of lactic acid bacteria belonging to genera *Enterococcus, Lactobacillus, Lactococcus, Streptococcus, Pediococcus, Leuconostoc*, and *Bifidobacterium*.
(9) The composition according to any one of (1) to (8), wherein
the lactic acid bacterium is a lactic acid coccus.
(10) The composition according to any one of (1) to (9), wherein
the lactic acid bacterium is *Enterococcus faecalis*.
(11) The composition according to any one of (1) to (10), which is a composition for oral intake.

Advantageous Effects of Invention

According to the present invention, by activating signaling and the like dependently on TLR7 and Myd88 in a living organism, an RNA derived from a lactic acid bacterium comprised as an effective component can promote production of IL-12 and the like, or suppress production of TNF-α. Moreover, according to the present invention, a reduction in the immune function of the living organism is suppressed by stimulating the immune function, and an excessive enhancement of the immune function is suppressed without adversely influencing the living organism. Thus, the balance of the immune function can be adjusted. Furthermore, lactic acid bacteria have been contained in fermentation foods such as fermented milks from the past, and the dietary practice is long. Hence, the lactic acid bacterium according to the present invention is considered to be highly safe.

DESCRIPTION OF EMBODIMENTS

Figure 1:
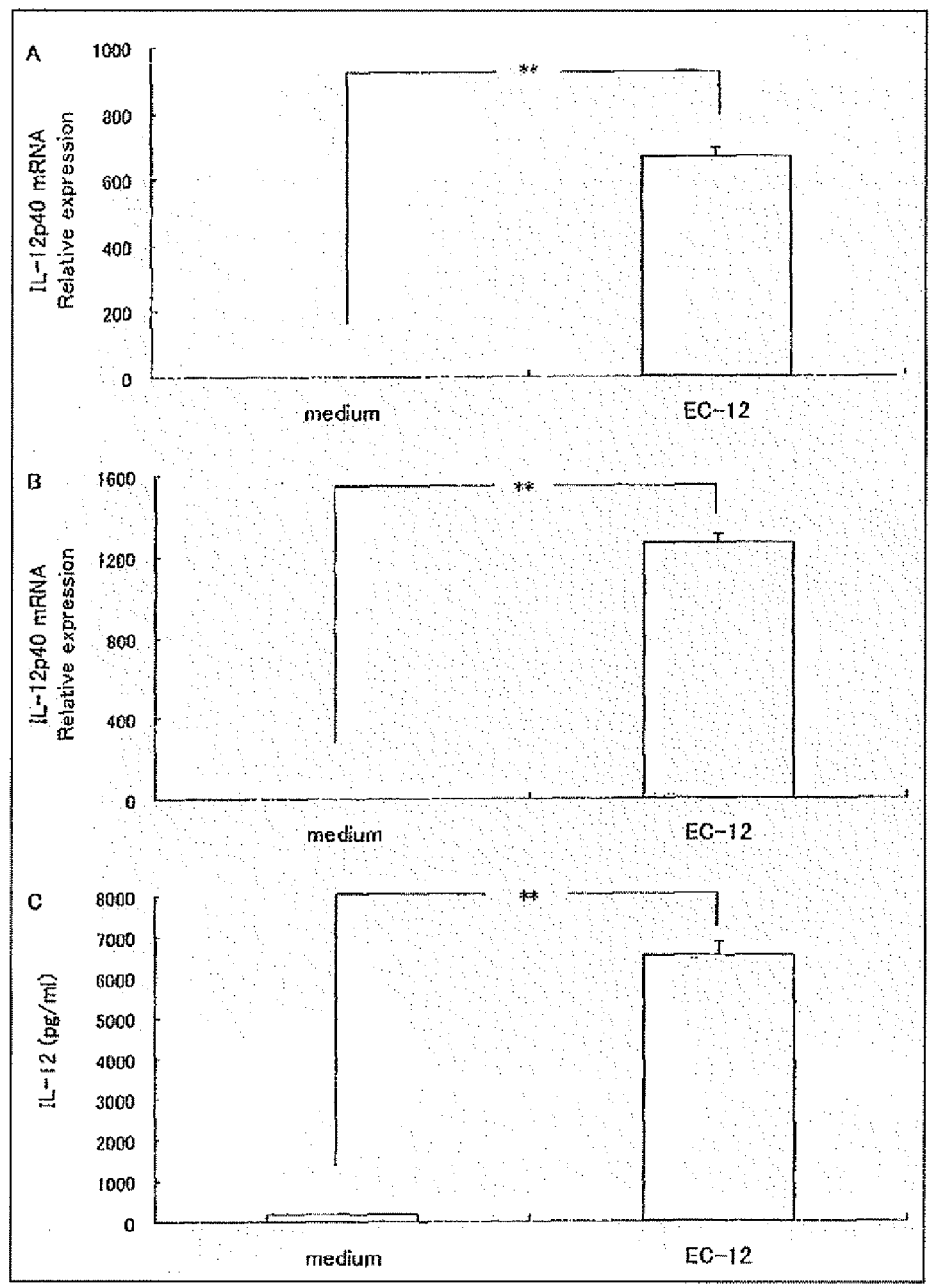
FIG. 1 shows bar graphs summarizing the result of culturing J774.1 cells with EC-12.

The present invention provides a composition having an immunomodulation action or a cytokine production-modulating action, and comprising an RNA derived from a lactic acid bacterium as an effective component.

In the present invention, the term "lactic acid bacterium" refers to a generic term of bacteria which produce lactic acid through lactic acid fermentation, that is, metabolism.

In the present invention, as the lactic acid bacterium, it is possible to use at least one or more lactic acid bacteria selected from the group consisting of lactic acid bacteria belonging to genera *Enterococcus, Lactobacillus, Lactococcus, Streptococcus, Pediococcus, Leuconostoc*, and *Eifidobacterium*.

Herein, examples of the bacteria belonging to the genus *Enterococcus* include *Enterococcus faecalis, Enterococcus faecium*, and so on.

Examples of the bacteria belonging to the genus *Lactobacillus* include *Lactobacillus acidophilus, Lactobacillus casei, Lactobacillus salivarius, Lactobacillus plantarum, Lactobacillus gasseri, Lactobacillus rhamnosus*, and so on.

Examples of the bacteria belonging to the genus *Lactococcus* include *Lactococcus cremoris, Lactococcus lactis*, and so on.

Examples of the bacteria belonging to the genus *Streptococcus* include *Streptococcus thermophilus*, and so on.

Examples of the bacteria belonging to the genus *Pediococcus* include *Pediococcus damnosus*, and so on.

Examples of the bacteria belonging to the genus *Leuconostoc* include *Leuconostoc mesenteroides*, and so on.

Examples of the bacteria belonging to the genus *Bifidobacterium* include *Bifidobacterium adolescentis*, *Bifidobacterium bifidum*, *Bifidobacterium breve*, *Bifidobacterium infantis*, *Bifidobacterium longum*, and so on.

In the present invention, the lactic acid bacterium may be a lactic acid coccus. Examples of the lactic acid coccus include *Enterococcus faecalis*, *Enterococcus faecium*, *Lactococcus cremoris*, *Lactococcus lactic*, *Streptococcus thermophilus*, and so on mentioned above, but are not necessarily limited thereto.

In the present invention, *Enterococcus faecalis* is preferably used as the lactic acid bacterium.

As *Enterococcus faecalis*, for example, bacterial strains such as *Enterococcus faecalis* EC-EC-12, ATCC 19433, ATCC 14508, ATCC 23655, IFO 16803, and IFO 16804 or variants thereof can be exemplified. Among the bacteria that can be utilized as the effective component, the EC-12 strain is the most preferable.

Herein, the "variant" is meant to include ones that those skilled in the art can obtain by a method well-known to those skilled in the art by which a specific bacterial strain is mutated within such a range that the change does not influence the natures of the strain, or ones that those skilled in the art can confirm as being equivalent thereto.

Note that *Enterococcus faecalis* EC-12 has been deposited at International Patent Organism Depositary, National Institute of Advanced Industrial Science and Technology (Central 6, 1-1-1, Higashi, Tsukuba, Ibaraki, postal code 305-5466, Japan) on February 25, Heisei 17 (2005) (original date of deposition). The accession number is FERM BP-10284.

In the present invention, the "RNA" may be of natural or non-natural origin. An RNA in a naturally-occurring state is a type of nucleic acid and is generally meant to be a linear polymer of certain ribonucleoside units, each ribonucleoside unit made up of a purine or pyrimidine base and a ribose sugar and linked to another nucleoside by a phosphodiester bond. In this context, the "linear" refers to the primary structure of the RNA. The RNA is generally single-stranded or double-stranded, but may also include a partially double-stranded RNA.

The effective component of the composition of the present invention is an RNA derived from a lactic acid bacterium, but is not particularly limited thereto. The RNA may be a single-stranded RNA, a double-stranded RNA, or a partially double-stranded RNA. Among these, from the viewpoint of being recognized by Toll-like receptor 7 (TLR7) in a living organism, a single-stranded RNA is preferable. Lactic acid bacteria have been contained in fermentation foods such as fermented milks from the past, and the dietary practice is long. Accordingly, the composition of the present invention comprising the RNA derived from the lactic acid bacterium as an effective component is considered to be highly safe. Note that, one type of the lactic acid bacterium may be used alone, or RNAs from two or more types of the lactic acid bacterium may be used in mixture. Further, with respect to the RNA, any RNA may be used regardless of the type of the RNA, for example, a messenger RNA (mRNA), a transfer RNA (tRNA), ribosomal RNA (rRNA), and other RNAs.

As the method for preparing the RNA of the lactic acid bacterium used as the effective component, conventionally used methods can be adopted. As the method for preparing the RNA of the lactic acid bacterium, for example, synthesis methods such as a nucleic acid synthesis method may be adopted, or methods by which the RNA is obtained from existing nucleic acid-supply sources (for example, a genomic DNA or a cDNA) may be adopted. Furthermore, examples of the method for preparing the RNA of the lactic acid bacterium include a phenol method, methods utilizing a spin column, glass filter, or ion exchange, and the like, but are not particularly limited to these methods.

In the present invention, the "immunomodulation action" means not only suppressing a reduction in the immune function of a living organism that intakes the composition of the present invent ion by stimulating the immune function, but also suppressing an excessively enhanced immune function such as allergic reaction. Hence, the immunomodulation action means an action of adjusting the balance of the immune function.

Moreover, the present invention also provides a composition having a cytokine production-modulating action, and comprising the RNA derived from the lactic acid bacterium as an effective component. In the present invention, examples of the "cytokine production-modulating action" include not only promoting production of at least one protein selected from the group consisting of IL-12, CCL2, CCL5, CCL7, CXCL10, IL-6, and IL-1α, but also suppressing an action of production of TNF-α.

In the present invention, IL-12 (Interleukin-12) may be IL-12p35, or IL-12p40, a heterodimer formed by these IL-12p70. Among these, IL-12p40 is preferable. Additionally, human-derived typical IL-12p35 includes a protein (gene) specified by ACCESSION No. NP_000873.2 (NM_000882.2). Human-derived typical IL-12p40 includes a protein (gene) specified by ACCESSION No. NP_002178.2 (NM_002187.2).

Moreover, in the present invention, a human-derived typical example of CCL2 (Chemokine (C-C motif) ligand 2) includes a protein (gene) specified by ACCESSION No. NP_002973.1 (NM_002982.3).

Further, in the present invention, a human-derived typical example of CCL5 (Chemokine (C-C motif) ligand 5) includes a protein (gene) specified by ACCESSION No. NP_002976.2 (NM_002985.2).

Furthermore, in the present invention, a human-derived typical example of CCL7 (Chemokine (C-C motif) ligand 7) includes a protein (gene) specified by ACCESSION No. NP_006264.2 (NM_006273.2).

Furthermore, in the present invention, a human-derived typical example of CXCL10 (Chemokine (C-X-C motif) ligand 10) includes a protein (gene) specified by ACCESSION No. NP_001556.2 (NM_001565.2).

Furthermore, in the present invention, a human-derived typical example of IL-6 (Interleukin-6, or also referred to as Interferon beta 2) includes a protein (gene) specified by ACCESSION No. NP_000591.1 (NM_000600.2).

Furthermore, in the present invention, a human-derived typical example of IL-1α (Interleukin-1 alpha) includes a protein (gene) specified by ACCESSION No. NP_000566.3 (NM_000575.3).

Furthermore, in the present invention, a human-derived typical example of TNF-α (Tumor necrosis factor-alpha) includes a protein (gene) specified by ACCESSION No. NP_000585.2 (NM_000594.2).

However, the amino acid sequence of the protein may be mutated in nature (i.e., unartificially). Thus, in the present invention, the cytokine such as IL-12 and TNF-α includes such a natural mutant.

Note that, in the present invention, the production of the cytokine such as IL-12 and TNF-α includes not only production of the protein itself, but also expression of a gene encoding each protein.

Further, in the present invention, the immunomodulation action or the cytokine production-modulating action is preferably an action dependent on at least one biomolecule selected from the group consisting of TLR7 and Myd88.

TLR7 is one type of the receptors, Toll-like receptors (TLRs), on macrophages and dendritic cells to recognize foreign microbes. TLR7 is expressed in an endosome in the cell and recognizes a virus-derived single-stranded RNA and the like. Moreover, Myd88 (myeloid differentiation primary response gene (88)) is an adapter protein which binds to a TIR domain of a corresponding Toll-like receptor (except for TLR3) in a cytoplasm and induces activation of NF-κB and MAPK when the receptor recognizes each ligand (a virus-derived single-stranded RNA and the like for TLR7)

In the present invention, a human-derived typical example of TLR7 includes a protein (gene) specified by ACCESSION No. NP_057646.1 (NM_016562.3). Moreover, a human-derived typical example of Myd88 includes a protein (gene) specified by ACCESSION No. NP_002459.2 (NM_002468.4).

However, the amino acid sequence of the protein may be mutated in nature (i.e., unartificially). Thus, in the present invention, the terms TLR7 and Myd88 include such a natural mutant, also.

An effective intake amount of the composition of the present invention in terms of RNA is 1 μg/kg/day to 10 mg/kg/day. Thus, the amount of the lactic acid bacterium contained in the composition of the present invention is set so that preferably 1 to 10000 mg in terms of a dry matter of the lactic acid bacterium can be taken per day, more preferably 10 to 1000 mg can be taken.

The composition of the present invention produces effects on intestinal function-regulating action, cancer risk-reducing action, prevention of atopic dermatitis, allergy reducing action, infection defense effect, and so forth.

The composition of the present invention can be suitably used as a composition for oral intake. As the composition for oral intake of the present invention, the RNA derived from the lactic acid bacterium can be directly used. Alternatively, the composition can be used in the form of the lactic acid bacterium directly. Further, it is also possible to use ones processed into preparations for oral administration such as a granule, a tablet, a capsule to all of which an excipient, a sweetener, a fragrance, a colorant, or the like may be added. In preparing a drug, generally-used additives for normal drugs, such as an excipient, a binder, a disintegrator, a lubricant, a stabilizer, a flavoring, a diluent, or a surfactant can be used as a preparation carrier. Moreover, in preparing a drug, a complex with a positively charged carrier such as a cationic liposome may be formed suitably for delivery to and incorporation into a target cell.

The specific form of the composition for oral intake of the present invention is not particularly limited. Examples thereof include one processed in general foods, confectionaries, jellies, gummies, candies, gums, snacks, baked confectioneries, retort pouch foods, convenience foods, dietary supplements, beverages, sheet-like foods, chewables, jelly beverages (chewable packs), paste products, porridges, foods boiled down in soy, and the like. Nonetheless, specific examples thereof are not limited thereto.

EXAMPLES

Hereinafter, the present invention will be more specifically described based on Examples and Test Examples. However, the present invention is not to be limited to Examples and the like below.

Test Example 1

Co-Culturing of J774.1 Cells and EC-12

<Maintenance of Mouse-Derived Macrophage-Like Cell J774.1 Strain>

A mouse-derived macrophage-like cell line, J774.1 cell line, was maintained in an RPMI 1640 medium (containing L-glutamine: manufactured by NACALAI TESQUE, INC.) containing 5% of fetal calf serum (FCS), 100 U/mL of penicillin, and 100 μg/mL of streptomycin under conditions of 5% $CO_2$ and 37° C. When reached 80% confluence, the cells were treated with a solution of 2.5 g/L trypsin and 1 mM EDTA (ethylene diamine tetraacetic acid) (manufactured by NACALAI TESQUE, INC.) for 5 minutes. Then, the cells were removed with a cell scraper (manufactured by IWAKI), and subcultured.

<Preparation of EC-12 for Addition>

As a lactic acid bacterium, dead cells of lactic acid bacterium EC-12 (manufactured by Combi Corporation) were added to an RPMI 1640 medium with 5% FCS such that the cell concentration was 10 mg/mL. To surely disperse the cells, the mixture was subjected to ultrasonication on ice using ULTRASONIC DISRUPTOR (manufactured by Tomy) at an output level of 3 with a disrupting period of 30 seconds and an intermission of 30 seconds five times for 2 minutes and 30 seconds in total. After the ultrasonication, the resulting cell suspension was diluted serially at three stages (10-fold, 10-fold, 5-fold) with an RPMI 1640 medium with 5% FCS, and the concentration was adjusted to 20 μg/mL for culturing.

<Culturing of J774.1 Cells with EC-12>

The J774.1 cells prepared as described above and having reached 80% confluence were washed with 0.1 M PBS (Phosphate buffered saline), followed by a treatment with a solution of 2.5 g/L trypsin-1 mM EDTA for 5 minutes. After the treatment, the cells were removed from the incubator with a cell scraper. The cell suspension thus obtained was centrifuged at 1,000 rpm (170 g) at room temperature for 5 minutes. The resulting accumulated cells were suspended again in an RPMI 1640 medium with 5% FCS. The number of the cells was counted using a hemocytometer, and the number of the cells was adjusted to $5 \times 10^5$ cells/mL. The cell suspension thus prepared was seeded into a 96-well plate for cell culturing (SUMILON: manufactured by Sumitomo Bakelite Co., Ltd.) by 100 μL/well ($5 \times 10^4$ cells), and precultured under conditions of 5% $CO_2$ and 37° C. for 4 hours until the cells adhered.

After the culturing, 100 μL of EC-12 for addition (20 μg/mL) prepared as described above was added to each well, and thereby the final concentration of EC-12 was 10 μg/mL. As the control, J774.1 cells cultured in a basal medium with no additional EC-12 were used. The culture period in all the experiments was 20 hours. The experimental procedure was conducted with a triplicate well for the control.

<RNA Extraction from Cells after Culturing for 20 Hours>

For extraction of total RNA from the cells, QUICKGENE RNA cultured cell HC kit S (manufactured by FUJIFILM Corporation) was used. An LRP solution (already supplemented with 10 μL/mL of 2-mercaptoethanol) attached to the kit was added by 100 μL/well, and transferred to screw cap tubes with 5-mm zirconia beads therein. Using FASTPREP FP120 (manufactured by Funakoshi Corporation), cells were disrupted at a speed of 4.0 for 40 seconds. To this, 15 μL of an SRP solution attached to the extraction kit was added and subjected to vortexing for 15 seconds. Then, 50 μL, of 99.5% ethanol was added thereto and subjected to vortexing for 1 minute. The subsequent treatment was carried out using QUICKGENE-Mini80 in accordance with the protocol attached to the kit. The DNase treatment was carried out by an on-column method using RNase free DNase I (manufactured by Takara) in accordance with the protocol attached to the kit.

<Synthesis of cDNA>

A reverse transcription reaction was carried out using the extracted RNA as a template and PrimeScript™ RT reagent Kit for Perfect Real Time (manufactured by Takara), and cDNA was synthesized. Specifically, the reverse transcription reaction was performed in accordance with the instruction attached to the kit using 150 ng of the total RNA as a template and Oligo dT Primer and Random 6 mers attached to the kit as reverse transcription primers while the total amount was adjusted to 10 μL with sterilized water (RNase free). Thus, cDNA was synthesized.

<Quantification of Amount of IL-12p40 Gene Expressed>

The amount of an IL-12p40 gene expressed was measured employing real-time PCR using the resulting synthesized cDNA as a template. For the real-time PCR, LIGHTCYCLER® 480 Real-Time PCR System (manufactured by Roche Applied Science) was used. The composition of the reaction solution was: 2 μL of the template cDNA, 5 μL of LIGHTCYCLER® 480 PROBEMASTER (manufactured by Roche Applied Science), 100-nM of Universal Probe Library Probe (manufactured by Roche Applied Science) and 200-nM of each primer. The total amount was 10 μL. The reaction was performed with 50 cycles each consisting of initial denaturing at 95° C. for 5 minutes, then 95° C. for 10 seconds, 60° C. for 10 seconds, and 72° C. for 10 seconds. Additionally, a glyceraldehyde-3-phosphate dehydrogenase (GAPDH) gene was used as an internal correction factor. The primers were designed using PROBEFINDER software (manufactured by Roche Applied Science). Table 1 shows the base sequence of each primer and Universal Probe Library Probe numbers. Moreover, LIGHTCYCLER® 480 software (manufactured by Roche Applied Science) was used for the analysis of the result of the real-time PCR. After the Threshold Cycle (Ct) value was calculated by the 2nd Derivative Maximum method, relative quantification analysis was conducted by the ΔΔCt method.

As apparent from the result shown in FIG. 1, the amount of the IL-12p40 gene expressed by the J774.1 cells cultured with EC-12 ("EC-12" of A and B in FIG. 1) was approximately 600 times for the first time (A in FIG. 1), and approximately 1200 times for the second time (B in FIG. 1), as large as the amount of the IL-12p40 gene expressed by the J774.1 cells with no additive ("medium" of A and B in FIG. 1). Moreover, the amount of the IL-12p40 protein produced by the J774.1 cells cultured with EC-12 ("EC-12" of C in FIG. 1) was approximately 35 times as large as the amount of the IL-12p40 protein produced by the J774.1 cells with no additive ("medium" of C in FIG. 1).

These results revealed that the culturing with EC-12 significantly increased both the amount of the IL-12p40 gene expressed and the amount of the IL-12p40 protein produced by the J774.1 cells (p<0.01). It was confirmed that EC-12 induced the macrophage to produce IL-12.

Test Example 2

DNase/RNase Treatment (Nuclease Treatment) on EC-12, and Culturing of Treated Bacterial Cells and J774.1 Cells EC-12 (10 mg/mL) dispersed in an RPMI 1640 medium with 5% FCS as described in <Preparation of EC-12 for addition> was treated with 20 units/mL of RNase free DNase I (manufactured by Takara) or 0.1 mg/mL of RNase A (manufactured by Invitrogen) at 37° C. for 30 minutes. After the treatment, EC-12 after each nuclease treatment was diluted at three stages as described above, and cultured with J774.1 cells in the same manner as in Test Example 1.

Moreover, as the control of the DNase and RNase treatments, LPS (Lipopolysaccharides from *Escherichia Coli* 0111:B4: manufactured by Sigma) was used. LPS adjusted to 10 μg/mL in an RPMI 1640 medium with 5% FCS was treated with a DNase or an RNase in the same manner as that for EC-12, and further diluted with an RPMI 1640 medium with 5% FCS to 0.6 μg/mL. Then, 100 μL of the resultant in each treatment was added to J774.1 cells, and thereby the final concentration of LPS was 0.3 μg/mL.

TABLE 1

| Gene name | | Primer sequence (5'-3') | (SEQ ID NO) | Probe No. |
|---|---|---|---|---|
| IL-12b (IL-12p40) | Forward | TGAACTGGCGTTGGAAGC | 1 | No. 74 |
| | Reverse | GCGGGTCTGGTTTGATGA | 2 | |
| GAPDH | Forward | TGTCCGTCGTGGATCTGAC | 3 | No. 80 |
| | Reverse | CCTGCTTCACCACCTTCTTG | 4 | |

<Quantification of IL-12 Protein>

The concentration of the IL-12 protein in the cell culture supernatant after the culturing for 20 hours was measured using Mouse Interleukin-12 ELISA Kit (BioSource: manufactured by Invitrogen). The measurement procedure followed the protocol of the kit.

FIG. 1 shows the thus-obtained result of the culturing of the J774.1 cells and EC-12. Note that, A and B in FIG. 1 show bar graphs for comparing the amount of the IL-12p40 gene expressed by the J774.1 cells, and C shows a graph for comparing the amount of the IL-12p40 protein produced by the 3774.1 cells. Moreover, ** (two asterisks) in FIG. 1 indicate p<0.01.

Figure 2:
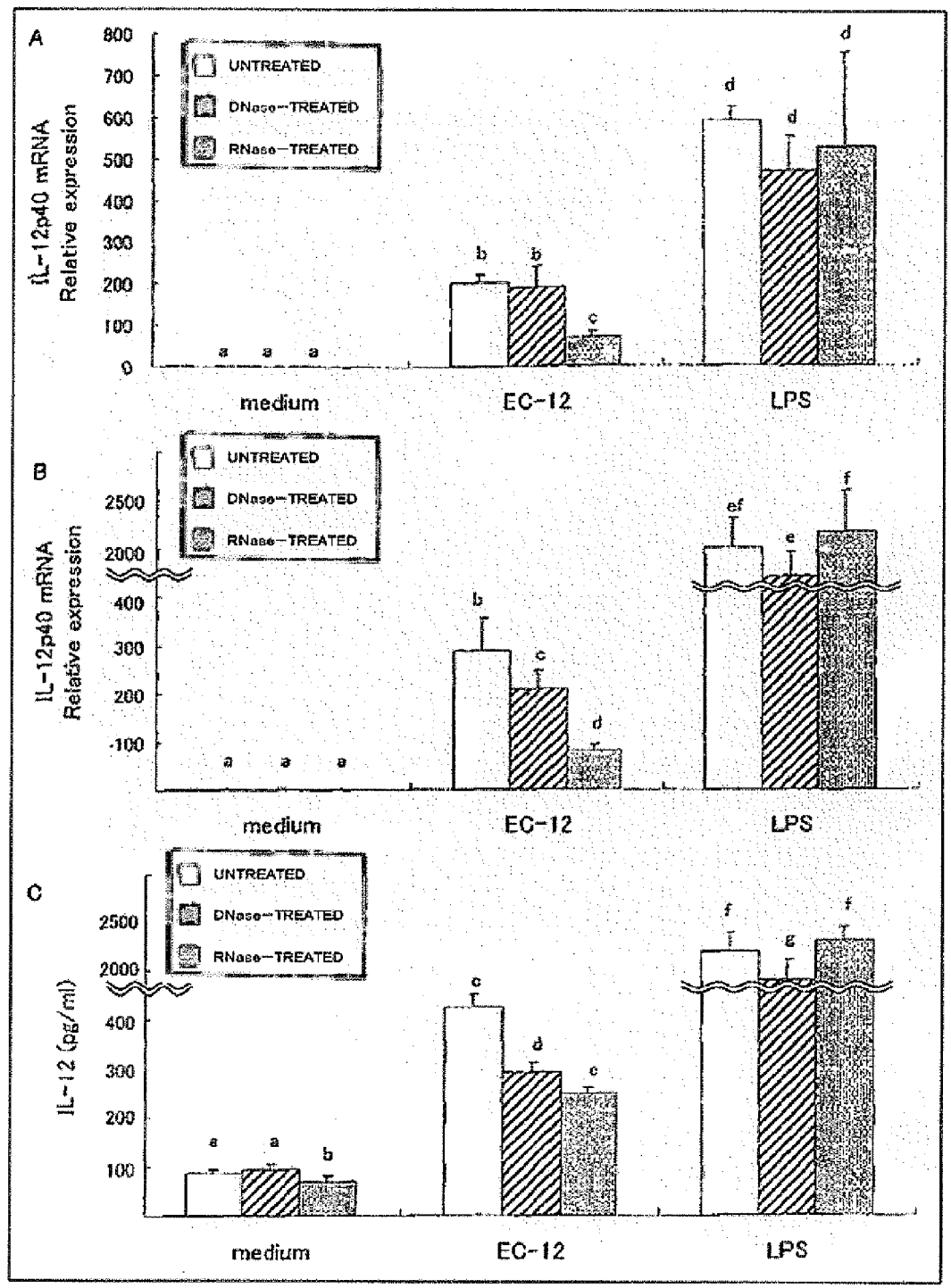
FIG. 2 shows bar graphs summarizing the result of culturing J774.1 cells with DNase-treated or RNase-treated EC-12 bacterial cells.

Subsequently, the amount of the IL-12p40 gene expressed by the cells after the culturing for 20 hours and the concentration of the IL-12 protein in the culture supernatant were measured in the same manner as in Test Example 1. FIG. 2 shows the obtained result. Note that A and B in FIG. 2 show bar graphs for comparing the amount of the IL-12p40 gene expressed by the J774.1 cells, and C in FIG. 2 shows graphs for comparing the amount of the IL-12 protein produced by the J774.1 cells (there were significant differences among different signs (a to g): p<0.05). Moreover, in the drawing, the bar graphs indicated by "medium" are graphs showing the result of the culturing of the J774.1 cells with no additional bacterium; and the bar graphs indicated by "EC-12" are graphs showing the result of the culturing of EC-12 and the J774.1 cells; and the bar graphs indicated by "LPS" are graphs showing the result of the culturing of LPS and the J774.1 cells.

As apparent from the result shown in FIG. 2, when evaluation was made with average values of the amount of the IL-12p40 gene expressed by the J774.1 cells cultured with untreated EC-12 (the values indicated by the white bar graphs in "EC-12" of A and B in FIG. 2) being set as 100%, the addition of RNase-treated EC-12 decreased the amount of the gene expressed to 94.1±25.7% for the first time (the value indicated by the hatched bar graph in "EC-12" of A in FIG. 2), and to 69.2±24.4% for the second time (the value indicated by the hatched bar graph in "EC-12" of B in FIG. 2). Further, the addition of RNase-treated EC-12 decreased the amount of the gene expressed to 33.8±1.2% for the first time (the value indicated by the black bar graph in "EC-12" of A in FIG. 2), and to 35.2±6.1% for the second time (the value indicated by the black bar graph in "EC-12" of B in FIG. 2).

Furthermore, when evaluation was made with an average value of the amount of the IL-12p40 protein produced by the J774.1 cells cultured with untreated EC-12 (the value indicated by the white bar graph in "EC-12" of C in FIG. 2) being set as 100%, the addition of DNase-treated EC-12 decreased the amount of the protein produced to 68.4±5.0% (the value indicated by the hatched bar graph in "EC-12" of C in FIG. 2), and the addition of RNase-treated EC-12 decreased the amount of the protein produced to 58.6±2.5% (the value indicated by the black bar graph in "EC-12" of C in FIG. 2). Note that there was no significant difference between RNase-treated and untreated in LPS used as the control.

These result revealed that when EC-12 was treated with either a DNase or an RNase, both the amount of the IL-12p40 gene expressed and the amount of the IL-12p40 protein produced by the J774.1 cells were significantly decreased in comparison with when untreated EC-12 was added. Particularly, a significant decrease was observed in the RNase treatment.

Figure 3:
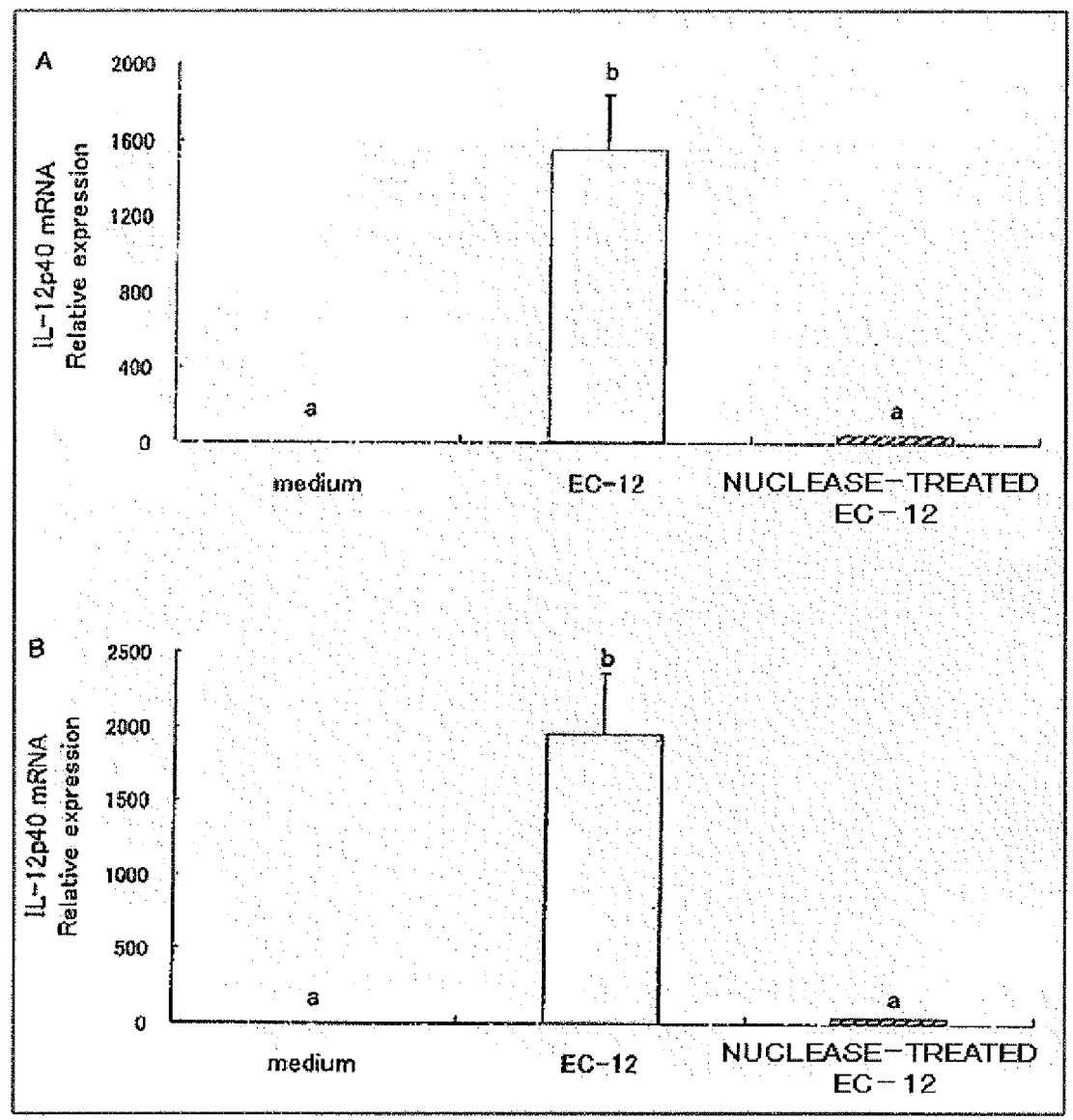
FIG. 3 shows bar graphs summarizing the result of culturing J774.1 cells with DNase-treated and RNase-treated EC-12 bacterial cells (nuclease-treated bacterial cells).

Meanwhile, separately from these, EC-12 was treated with both a DNase and an RNase (nuclease treatment), and cultured with J774.1 cells. Specifically, EC-12 dispersed in an RPMI 1640 medium with 5% FCS (10 mg/mL) was treated with both 20 units/mL of RNase free DNase I (manufactured by Takara) and 0.1 mg/mL of RNase A (manufactured by Invitrogen) at 37° C. for 30 minutes. After the treatment, the EC-12 samples were diluted at three stages in the same manner as in Test Example 1, and cultured with J774.1 cells. The amount of the IL-12p40 gene expressed by such cells was measured. FIG. 3 shows the obtained result. Both A and B in FIG. 3 show bar graphs for comparing the amount of the IL-12p40 gene expressed by the J774.1 cells (there was a significant difference between different signs (a and b): $p<0.01$). Moreover, in FIG. 3, the bar graphs indicated by "medium" are graphs showing the result of the culturing of the J774.1 cells with no additive; the bar graphs indicated by "EC-12" are graphs showing the result of the culturing of EC-12 and the J774.1 cells; and the bar graphs indicated by "nuclease-treated EC-12" are graphs showing the result of the culturing of DNase-treated and RNase-treated EC-12 and the J774.1 cells.

As apparent from the result shown in FIG. 3, when evaluation was made with average values of the amount of the IL-12p40 gene expressed by the J774.1 cells cultured with untreated EC-12 (the values indicated by the white bar graphs in "EC-12" of A and B in FIG. 3) being set as 100%, the addition of EC-12 treated with both the DNase and the RNase significantly decreased the amount of the gene expressed to 3.0±0.1% for the first time (the value indicated by the hatched bar graph in "nuclease-treated EC-12" of A in FIG. 3), and 2.1±0.2% for the second time (value indicated by the hatched bar graph in "nuclease-treated EC-12" of B in FIG. 3) ($p<0.01$).

Such a result revealed that the treatment with both the DNase and the RNase almost abolished the ability to induce IL-12p40 production exhibited by EC-12. Together with the above-described result obtained when EC-12 treated with either the DNase or the RNase was added, it was suggested that the main component of EC-12 inducing the macrophage to produce IL-12 was a nucleic acid, particularly an RNA.

Test Example 3

Culturing of J774.1 Cells and EC-12 Under Inhibition of TLR7 or TLR9 Signaling

Phosphorothioated (S-modified) synthetic oligonucleotides (ODNs) were used as antagonists of TLR7 and TLR9 (see Barrat, F. J. et al. J. Exp. Med. 2005, 202(8): 1131-9). Specifically, IRS661 was used as the antagonist of TLR7, and IRS869 was used as the antagonist of TLR9. Moreover, CL097 (manufactured by InvivoGen) was used as an agonist of TLR7, and a phosphorothioated synthetic ODN, ISS1018, was used as an agonist of TLR9. Table 2 shows the sequence of each synthetic ODN.

TABLE 2

| | Sequence | (SEQ ID NO) |
|---|---|---|
| IRS661 (TLR7 antagonist) | TsGsCsTsTsGsCsAsAsGsCsTsTsGsCsAsAsGsCsA | 5 |
| IRS869 (TLR9 antagonist) | TsCsCsTsGsGsAsGsGsGsGsTsTsGsT | 6 |
| ISS1018 (TLR9 agonist) | TsGsAsCsTsGsTsGsAsAsCsGsTsTsCsGsAsGsAsTsGsA | 7 |

*s = S-modified (phosphorothioated) phosphorylation site

Thirty minutes before the aforementioned 20-hour culturing was started, IRS661 and IRS869 were added to media in such a manner that the amounts were 5.6 µM and 0.7 µM, respectively, and cultured in a $CO_2$ incubator. Then, culturing with EC-12 was performed in the same manner as in Test Example 1. Moreover, ISS1018 and CL097 were added to the media in such a manner as to achieve 0.7 µM and 1 µg/mL, respectively, which were cultured for 20 hours and used as controls for confirming inhibition by the antagonists.

Figure 4:
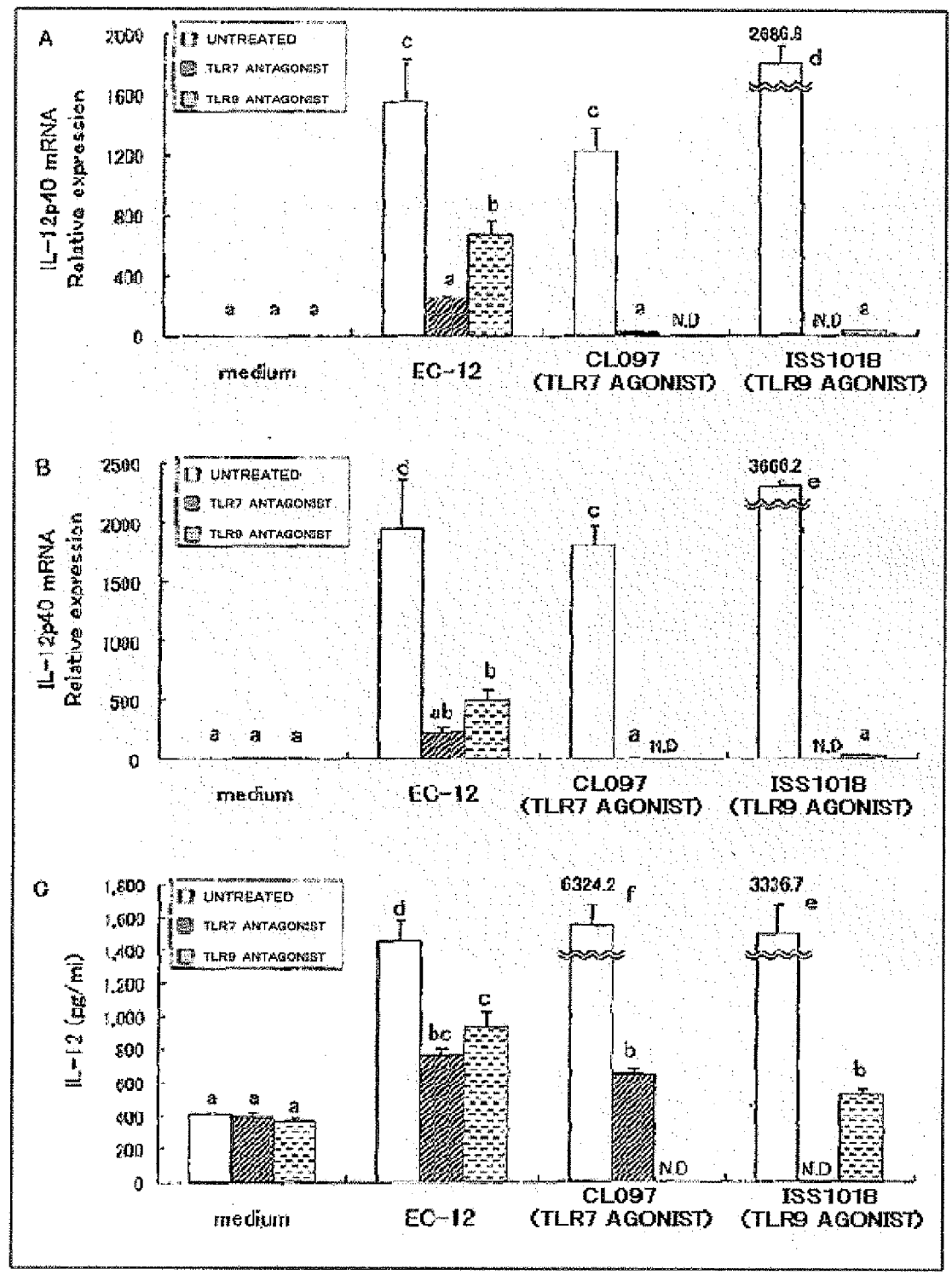
FIG. 4 shows bar graphs summarizing the result of inhibition of TLR7•TLR9 signaling in J774.1 cells and culturing with EC-12.

Subsequently, the amount of the IL-12p40 gene expressed by the cells cultured in the presence of the antagonist or agonist and the concentration of the IL-12p40 protein in the culture supernatant were measured in the same manner as in Test Example 1. FIG. 4 shows the obtained result. Note that both A and B in FIG. 4 show bar graphs for comparing the amount of the IL-12p40 gene expressed by the J774.1 cells, and C in FIG. 4 shows graphs for comparing the amount of the IL-12 protein produced by the J774.1 cells (there were significant differences among different signs (a to f): p<0.05). Moreover, in the graphs of FIG. 4, "N. D." means "No Data", that is, no measurement was performed. Further, in the drawing, the bar graphs indicated by "medium" are graphs showing the result of the culturing of the J774.1 cells with no additional bacterium; the bar graphs indicated by "EC-12" are graphs showing the result of the culturing of EC-12 and the J774.1 cells; the bar graphs indicated by "CL097 (TLR7 agonist)" are graphs showing the result of the culturing of the TLR7 agonist and the J774.1 cells; the bar graphs indicated by "ISS1018 (TLR9 agonist)" are graphs showing the result of the culturing of the TLR9 agonist and the J774.1 cells.

First, as apparent from the result shown in the three bar graphs indicated by "CL097 (TLR7 agonist)" and the three bar graphs indicated by "ISS1018 (TLR9 agonist)" of A to C in FIG. 4, it was confirmed that the addition of the TLR7 antagonist or the TLR9 antagonist significantly decreased the amount of the IL-12p40 gene expressed and the amount of the protein produced attributable to the TLR7 agonist and the TLR9 agonist (p<0.05). It was confirmed that the TLR7 antagonist and the TLR9 antagonist appropriately inhibited each of TLR7 and TLR9 signaling.

Next, as apparent from the result shown in the three bar graphs indicated by "EC-12" of A and B in FIG. 4, when evaluation was made with average values of the amount of the IL-12p40 gene expressed by the J774.1 cells cultured with untreated EC-12 (the values indicated by the white bar graphs in "EC-12" of A and B in FIG. 4) being set as 100%, the addition of the TLR7 antagonist decreased the amount of the gene expressed to 16.0±1.0% for the first time (the value indicated by the hatched bar graph in "EC-12" of A in FIG. 4), and to 11.5±2.4 for the second time (the value indicated by the hatched bar graph in "EC-12" of B in FIG. 4). Meanwhile, the addition of the TLR9 antagonist decreased the amount of the gene expressed to 43.7±6.0% for the first time (the value indicated by the bar graph with horizontal lines in "EC-12" of A in FIG. 4), and to 25.4±4.8% for the second time (the value indicated by the bar graph with horizontal lines in "EC-12" of B in FIG. 4).

Furthermore, as apparent from the result shown in the three bar graphs indicated by "EC-12" of C in FIG. 4, when evaluation was made with average values of the amount of the IL-12 protein produced by the J774.1 cells cultured with untreated EC-12 (the values indicated by the white bar graphs in "EC-12" of C in FIG. 4) being set as 100%, the addition of the TLR7 antagonist decreased the amount of the protein produced to 51.9±3.1% (the value indicated by the hatched bar graph in "EC-12" of C in FIG. 4). Meanwhile, the addition of the TLR9 antagonist decreased the amount of the protein produced to 63.9±6.5% (the value indicated by the bar graph with horizontal lines in "EC-12" of C in FIG. 4).

From the above, it was revealed that the addition of the TLR7 antagonist or the TLR9 antagonist significantly decreased the amount of the IL-12p40 gene expressed by the J774.1 cells induced by EC-12 (p<0.05). In addition, it was revealed that in comparison with the case where the TLR9 signaling was inhibited, the ability to induce IL-12p40 production exhibited by EC-12 was significantly suppressed in the case where the TLR7 signaling was inhibited. This corresponded to the result demonstrated in Test Example 2 that the amount of IL-12p40 produced when RNase-treated EC-12 was added was smaller than the amount of IL-12p40 produced when DNase-treated EC-12 was added, thus strongly suggesting that the effective component of EC-12 inducing IL-12 production from the J774.1 cells was a nucleic acid, particularly an RNA.

Moreover, as apparent from the result shown in FIGS. 2 and 4, the percentage decrease in the ability to induce IL-12p40 production attributable to the RNase-treated EC-12 and the percentage decrease in the ability to induce IL-12p40 production attributable to the inhibition of the TLR7 signaling almost corresponded to each other in both the amount of the gene expressed and the amount of the protein produced.

Test Example 4

Nucleic Acid Extraction from EC-12, and Culturing of Extracted Nucleic Acid and J774.1 Cells <RNA Extraction from EC-12>

An RNA was extracted from EC-12, using QUICKGENE RNA tissue kit S II (manufactured by FUJIFILM Corporation). Specifically, 500 µL of an LRT solution (already supplemented with 10 µL/mL of 2-mercaptoethanol) attached to the kit was added to 150 mg of EC-12, and transferred to screw cap tubes with 0.1-mm glass beads therein. Using FASTPREP FP120 (manufactured by Funakoshi Corporation), the mixture was homogenized at a speed of 6.5 for 90 seconds. The subsequent operation was carried out in accordance with the extraction protocol of the kit. Meanwhile, the DNase treatment was carried out by an on-column method using RNase free DNase I (manufactured by Takara) according to the protocol attached to kit S II above.

<DNA Extraction from EC-12>

A DNA was extracted from EC-12 using QUICKGENE DNA tissue kit S (manufactured by FUJIFILM Corporation) in accordance with QUICKGENE Application Guide No. 38. Specifically, 250 µL of an MDT solution attached to the kit was added to 150 mg of EC-12, and transferred to screw cap tubes with 0.1-mm glass beads therein. Using FASTPREP FP120 (manufactured by Funakoshi Corporation), the mixture was homogenized at a speed of 6.5 for 90 seconds. Then, 25 µL of an EDT solution attached to the kit was added thereto, followed by incubation at 55° C. for 60 minutes. After the incubation, the resultant was centrifuged at 13,000 rpm (12,000 g) at room temperature for 10 minutes. Subsequently, 200 µL of the supernatant was sorted into another microtube to which 60 µL of RNase A (20 mg/mL: manufactured by Invitrogen) was added, followed by incubation at room temperature for 2 minutes. Further, 180 µL of an LDT solution attached to the kit was added thereto and subjected to vortexing for 15 seconds, followed by incubation at 70° C. for 10 minutes. To this, 240 µL of 99.5% ethanol was added and subjected to vortexing for 15 seconds. The subsequent treatment was carried out using QUICKGENE-Mini80 in accordance with the protocol attached to the kit.

Figure 5:
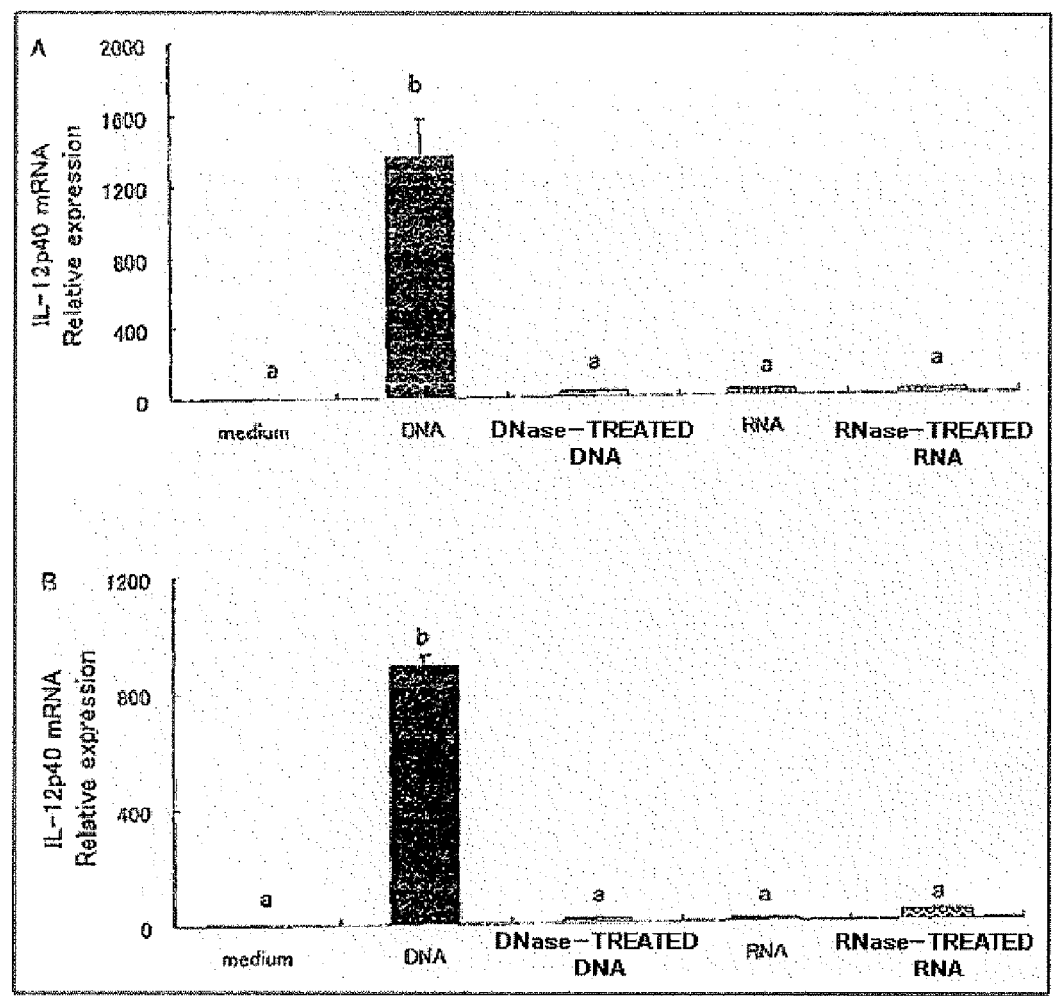
FIG. 5 shows bar graphs summarizing the result of culturing J774.1 cells and a nucleic acid extracted from EC-12.

After the extraction, each of the RNA and the DNA was mixed into an RPMI 1640 medium with 5% FCS. The RNA and the DNA were added to the media in such a manner as to achieve 5.6 ng/µL and 4.6 ng/µg, respectively, and cultured with J774.1 cells. The expression of the IL-12p40 gene in the cells after the culturing was quantified in the same manner as in Test Example 1. FIG. 5 shows the obtained result. Note that both A and B in FIG. 5 show bar graphs for comparing the amount of the IL-12p40 gene expressed by the J774.1 cells (there was a significant difference between different signs (a and b): p>0.01). Moreover, in FIG. 5, the bar graphs indicated by "medium" are graphs showing the result of the culturing of the 3774.1 cells with no additive; the bar graphs indicated by "DNA" are graphs showing the result of the culturing of the DNA extracted from EC-12 and the J774.1 cells; the bar graphs indicated by "RNase-treated DNA" are graphs showing the result of the culturing of the DNase-treated DNA of EC-12 and the J774.1 cells; the bar graphs indicated by "RNA" are graphs showing the result of the culturing of the RNA extracted from EC-12 and the J774.1 cells; and the bar graphs indicated by "RNase-treated RNA" are graphs showing the result of the culturing of the RNase-treated RNA of EC-12 and the J774.1 cells.

As apparent from the result shown in the bar graphs of "medium" and the bar graphs of "DNA" in FIG. 5, it was confirmed that the addition of the DNA extracted from EC-12 increased the amount of the IL-12p40 gene expressed by the J774.1 cells approximately 1300 times for the first time (A in FIG. 5), and approximately 900 times for the second time (B in FIG. 5), as large as that with no addition. Moreover, as apparent from the result shown in the bar graphs of "DNase-treated DNA," it was confirmed that no enhancement of the amount of the IL-12p40 gene expressed was observed by the treatment of the DNA with the DNase.

Meanwhile, the comparison between the bar graphs of "medium" and the bar graphs of "RNA" revealed that no change in the amount of the IL-12p40 gene expressed by the J774.1 cells was observed by the addition of the RNA extracted from EC-12. Moreover, the result shown in the bar graphs of "RNase-treated RNA" similarly revealed that no change was observed even when the RNA was treated with the RNase.

The above result confirmed that the J774.1 cells certainly recognized the DNA as an antigen. Meanwhile, the addition of the RNA extracted from EC-12 hardly changed the IL-12p40 production by the J774.1 cells. Accordingly, by taking into account findings that TLR7 and TLR9 are expressed in an endosome in a cell (see Nishiya, T. et al. J. Biol. Chem. 2005, 4; 280 (44): 37107-17, and Leifer, C. A. et al. J. Immunol. 2004, 173 (2): 1179-83), it seems to be necessary to incorporate free DNA molecule or RNA molecule into a cell so that TLR7 and TLR9 can recognize such free DNA molecule or RNA molecule. There is a report that a macrophage incorporates a bacterium-derived DNA through a scavenger receptor (see Zhu, F. G. et al. Immunology. 2001, 103 (2): 226-34). However, there has been no report on a mechanism to incorporate an RNA. It is assumed that a free DNA is incorporated into a cell through a scavenger receptor and recognized by TLR9. Nonetheless, a macrophage does not have a mechanism to incorporate an RNA. This suggests a possibility that a free RNA is not incorporated into the cell and not recognized as an antigen.

Example 1

Lipofection of RNA Derived from EC-12 Into J774.1 Cells

Since it was inferred that the J774.1 cell did not incorporate a free RNA, lipofection was performed to introduce the RNA into the cell. For the lipofection, FuGENE HD Transfection Reagent (manufactured by Roche Applied Science) was used. Total RNA was extracted from EC-12 and prepared in the same manner as in Test Example 4. The concentration thereof was adjusted to 20 μg/μL with a serum-free medium (Opti-MEM). Then, 6 μL of FuGENE HD Transfection Reagent was added thereto and reacted for 10 minutes to form a FuGENE/RNA complex. This complex was added dropwise by 5 μL/0.5×$10^5$ cells, and cultured for 20 hours. Moreover, total RNA (50 μg/μL) derived from EC-12 was treated with 0.1 mg/mL of RNase A (manufactured by Invitrogen), and was also subjected to lipofection by the same method. Further, J774.1 cells having TLR7 signaling inhibited were prepared in the same manner as in Test Example 3. The resulting prepared cells were also subjected to lipofection by the same method.

Figure 6:
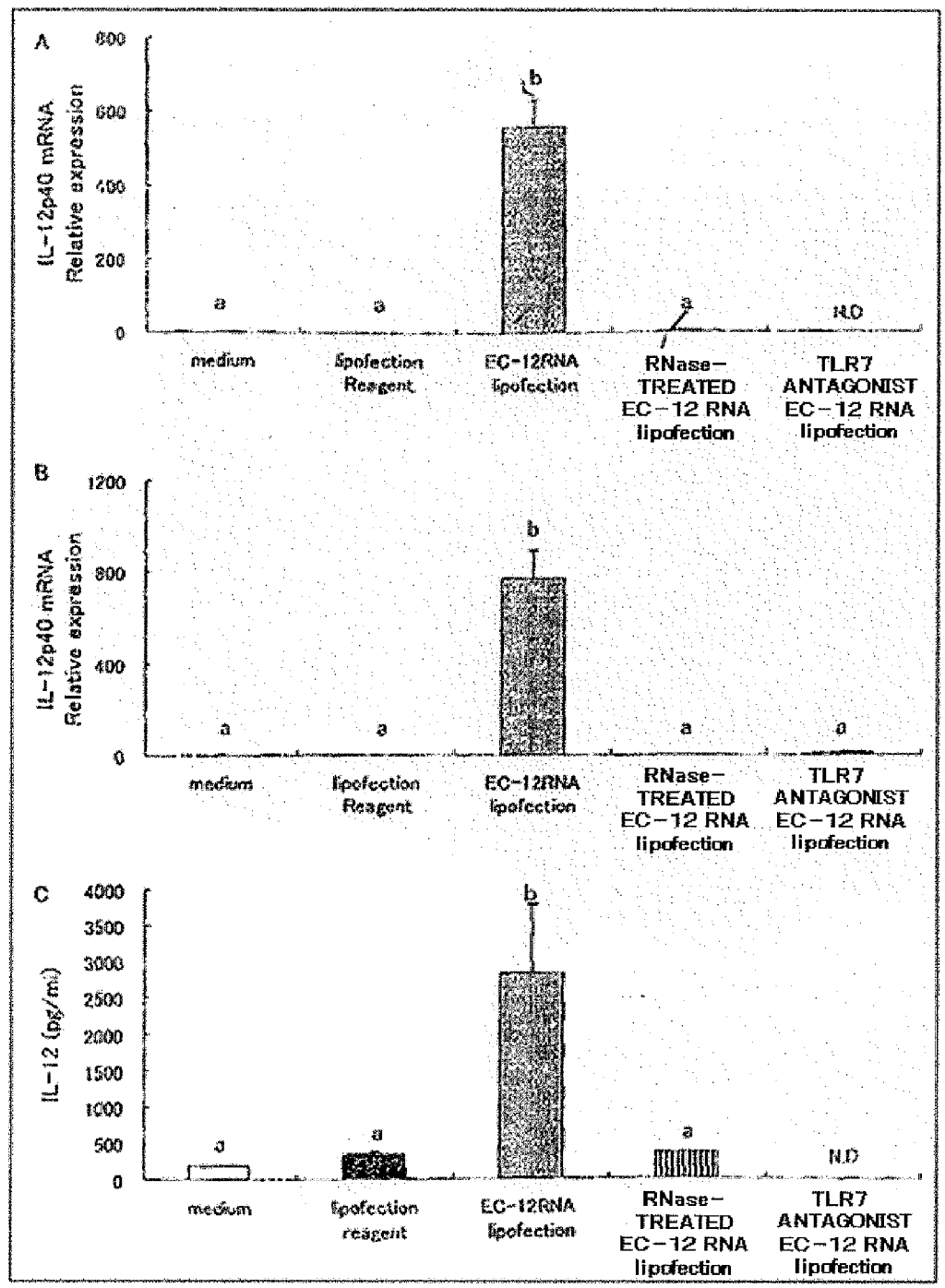
FIG. 6 shows bar graphs summarizing the result of lipofection of an RNA derived from EC-12 into J774.1 cells.

Subsequently, the amount of the IL-12p40 gene expressed by these cells and the concentration of the IL-12 protein in the culture supernatant were measured in the same manner as in Test Example 1. FIG. 6 shows the obtained result. Note that both A and B in FIG. 6 show bar graphs for comparing the amount of the IL-12p40 gene expressed by the J774.1 cells, and C in FIG. 6 shows a graph for comparing the amount of the IL-12p40 protein produced by the J774.1 cells (there was a significant difference between different signs (a and b): $p<0.01$). In the graphs, "N. D." means "Not Determined", that is, no detection was achieved. Moreover, in the drawing, the bar graphs indicated by "medium" are graphs showing the result of the culturing of the J774.1 cells with no additive; the bar graphs indicated by "lipofection Reagent" are graphs showing the result of the culturing of the lipofection reagent and the J774.1 cells; the bar graphs indicated by "EC-12 RNA lipofection" are graphs showing the result of the culturing of the lipofected RNA of EC-12 and the J774.1 cells; the bar graphs indicated by "RNase-treated EC-12 RNA lipofection" are graphs showing the result of the culturing of the RNA of EC-12 subjected to the lipofection after the RNase treatment and the J774.1 cells; the bar graphs indicated by "TLR7 antagonist EC-12 RNA lipofection" are graphs showing the result of the culturing of the lipofected RNA of EC-12 and the J774.1 cells having TLR7 signaling inhibited.

The result shown in the bar graphs of "medium" and the bar graphs of "EC-12 RNA lipofection" in FIG. 6 revealed that the lipofection of the RNA extracted from EC-12 increased the amount of the IL-12p40 gene expressed by the J774.1 cells approximately 600 times for the first time (A in FIG. 6), and approximately 800 times for the second time (B in FIG. 6), as large as that with no addition, and increased the amount of the IL-12p40 protein produced by the J774.1 cells approximately 15 times (C in FIG. 6) as large as that with no addition.

Moreover, the comparison between the bar graphs of "lipofection Reagent" in FIG. 6 and the bar graphs of "EC-12 RNA lipofection" revealed that the lipofection of the RNA extracted from EC-12 increased the amount of the IL-12p40 gene expressed by the J774.1 cells approximately 400 times for the first time (A in FIG. 6), approximately 400 times for the second time (B in FIG. 6), as large as that of the cells on which only the lipofection reagent was effected. Moreover, it was also revealed that the RNA derived from EC-12 increased the amount of the IL-12 protein produced by the J774.1 cells approximately 8 times (C in FIG. 6) as large as that with no addition.

Further, from the result shown in the bar graphs of "RNase-treated EC-12 RNA lipofection" and the bar graphs of "TLR7 antagonist EC-12 RNA lipofection", it can be seen that the RNase treatment on the RNA or inhibition of the J774.1 cells from TLR7 signaling almost abolished the induction to express the IL-12p40 gene by the J774.1 cells attributable to the lipofection of the RNA derived from EC-12.

These results revealed the J774.1 cells recognized the RNA as an antigen in the cells (FIG. 6). Moreover, the introduction of the RNA into the cells having TLR7 signaling inhibited did not lead to induction of IL-12p40 production. This suggests that the RNA derived from EC-12 is recognized by TLR7 in the cell and the gene expression is induced. Thus, it is conceivable that after EC-12 is incorporated in a cell, an RNA in EC-12 is recognized as an antigen by TLR7 in the cell.

Meanwhile, a ligand recognized by TLR7 is generally a virus-derived single-stranded RNA (see Lund, J. M. et al. Proc. Natl. Acad. Sci. USA. 2004, 101(15): 5598-603). Nevertheless, the above-described results revealed in the first place that the bacterium-derived RNA was recognized by TLR7.

Test Example 5

Change in Ability to Induce IL-12 Production by J774.1 Cells By Culturing with Each Bacterium Treated with RNase or DNase Bacterial cells (*Enterococcus faecalis* EC-12, *Enterococcus faecalis* (different strain), *Enterococcus faecium*, *Lactococcus cremoris*, *Lactococcus lactis*, *Streptococcus thermophilus*, *Lactobacillus casei*, *Lactobacillus gasseri*, *Lactobacillus plantarum*, *Lactobacillus rhamnosus*, *Lactobacillus salivarius*, *Bifidobacterium adolescentis*, *Bifidobacterium bifidum*, *Bifidobacterium breve*, *Bifidobacterium infantis*, and *Bifidobacterium longum*) were prepared by a RNase treatment (with 0.1 mg/ml of RNase (manufactured by Invitrogen) at 37° C. for 30 minutes), or by a DNase-treatment (with 20 units/ml of RNase free DNase I (manufactured by Takara) at 37° C. for 30 minutes), and used in the experiment.

Figure 7:
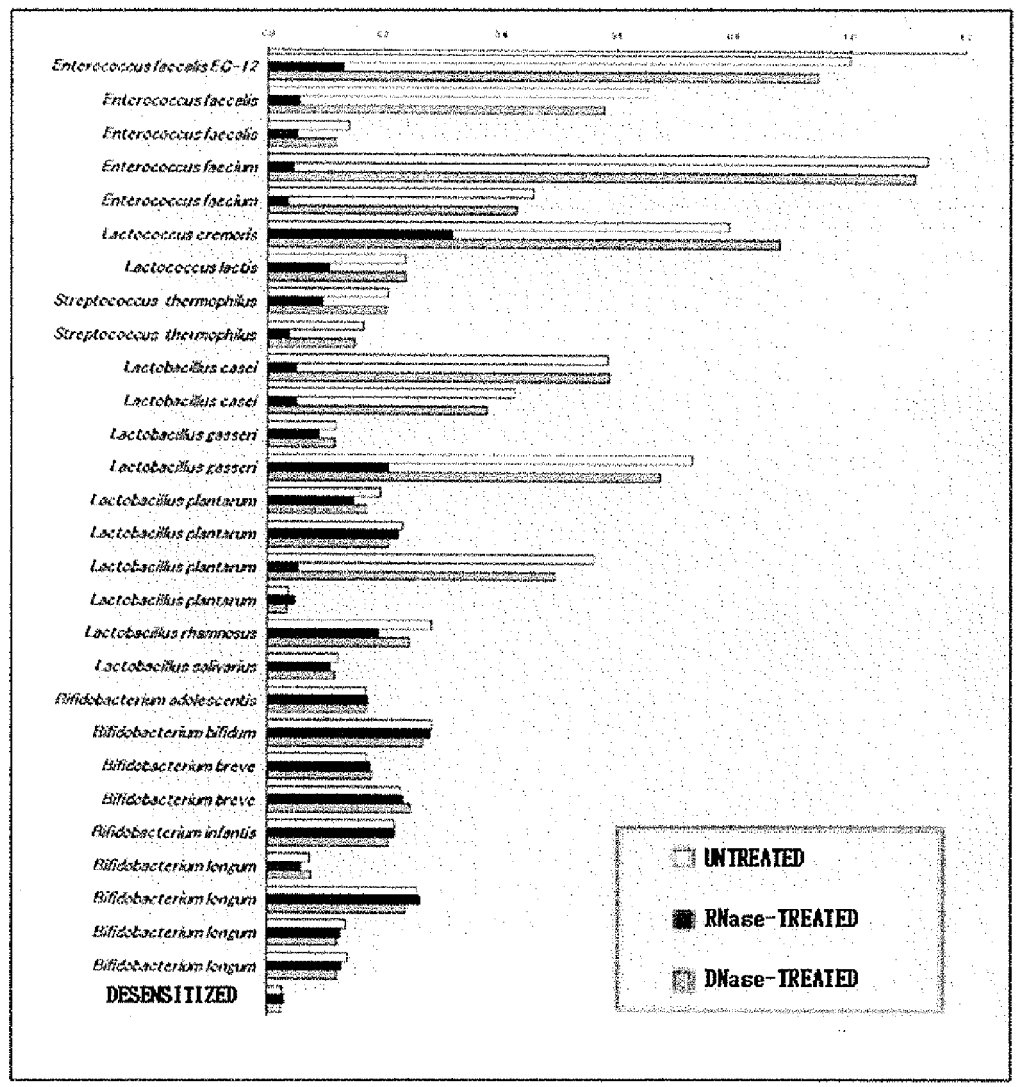
FIG. 7 shows bar graphs summarizing an ability to induce IL-12 production of bacterial cells of each lactic acid bacterium.

J774.1 cells was sensitized to the prepared bacterial cells, RNase-treated bacterial cells and DNase-treated bacterial cells at the final concentration of 10 µg/ml, and the concentration of the IL-12 protein was measured. In addition, similarly the protein concentration of desensitized J774.1 cells as the control was measured. Note that the concentration of IL-12 protein in the culture supernatant was measured in the same manner as in Test Example 1. The induction of IL-12 production in each bacterial cell was expressed as a relative value to the value of the result of untreated *Enterococcus faecalis* EC-12 set as 1.00 (reference value). FIG. 7 shows the obtained result. Note that FIG. 7 shows the result obtained when the untreated bacterial cells (upper white bar graph), the RNase-treated bacterial cells (middle black bar graph), and the DNase-treated bacterial cells (lower hatched bar graph) were used regarding the ability to induce IL-12 production of each bacterial cell of *Enterococcus faecalis* EC-12, *Enterococcus faecalis* (different strain), *Enterococcus faecium*, *Lactococcus cremoris*, *Lactococcus lactis*, *Streptococcus thermophilus*, *Lactobacillus casei*, *Lactobacillus gasseri*, *Lactobacillus plantarum*, *Lactobacillus rhamnosus*, *Lactobacillus salivarius*, *Bifidobacterium adolescentis*, *Bifidobacterium bifidum*, *Bifidobacterium breve*, *Bifidobacterium infantis*, and *Bifidobacterium longum*. Additionally, the result shows two examples for each of *Enterococcus faecium*, *Streptococcus thermophilus*, *Lactobacillus casei*, *Lactobacillus gasseri*, and *Bifidobacterium breve*, three examples for *Enterococcus faecalis*, and four examples for each of *Lactobacillus plantarum* and *Bifidobacterium longum*. These are the result for each bacterium of the same species but different strains.

As apparent from the result shown in FIG. 7, in *E. faecalis*, *E. faecium*, *L. cremoris*, *L. lactis*, *S. thermophilus* which were lactic acid cocci, almost no difference was observed between the values obtained by using the untreated bacterial cells and the values obtained by using the DNase-treated bacterial cells. In contrast, it was revealed that the values obtained by using the RNase-treated bacterial cells were ½ to ¹⁄₃₀ of the values obtained by using the untreated bacterial cells or the DNase-treated bacterial cells and significantly lowered. This shows that RNase treatment significantly lowered the ability to induce IL-12 production of the lactic acid cocci. Particularly, when *E. faecalis*, *E. faecium*, *L. cremoris*, *L. lactis*, and *S. thermophilus* were used, the same results were obtained in several strains.

Meanwhile, it was also revealed that in *L. casei*, *L. gasseri*, *L. plantarum*, *L. rhamnosus*, and *L. salivarius* which were lactic acid bacilli, although there were differences among the strains, the values obtained by using the RNase-treated bacterial cells were generally lower than the values obtained by using the untreated bacterial cells or the DNase-treated bacterial cells. Particularly, when *L. casei* was used, significant lowering in the values obtained by using the RNase-treated bacterial cells was observed in the two examples of the different strains. Meanwhile, when *L. plantarum* was used, significant lowering in the values obtained by using the RNase-treated bacterial cells was observed particularly in the third example from the top. This shows that when the lactic acid bacilli were used as the lactic acid bacterium, although there were differences among the bacterial species and strains, generally the RNase treatment significantly lowered the ability to induce IL-12 production.

Note that in the four bacterial species belonging to the genus *Bifidobacterium* examined this time, the amount of IL-12 production was not observed to be lowered by the RNase treatment.

As described above, when lactic acid bacteria such as *E. faecalis*, *E. faecium*, *L. cremoris*, *L. lactis*, *S. thermophilus*, *L. casei*, *L. gasseri*, *L. plantarum*, *L. rhamnosus*, and *L. salivarius* were RNase-treated, the ability to induce IL-12 production by the J774.1 cells significantly decreased in comparison with that when the untreated bacterial cells were added. This revealed that the ability to induce IL-12 production by the J774.1 cells was enhanced not only by the RNA derived from EC-12, but also by the RNAs derived from the lactic acid bacteria.

Test Example 6

Analysis Using Knockout Mice

To specify the above-described mechanism to induce IL-12 production attributable to an RNA derived from a lactic acid bacterium, spleen cells were isolated from Myd88-, TLR2-, or TLR4-knockout mice, and evaluated using lactic acid bacterial strains (EC-12, five strains of *Lactobacillus*, and five strains of *Enterococcus*) shown in Table 3. Moreover, spleen cells were isolated from a TLR7-knockout mouse, and evaluated using EC-12.

TABLE 3

| No. | Bacterium | Strain |
|---|---|---|
| 1 | Enterococcus faecalis | ATCC14508 |
| 2 | Enterococcus faecalis | ATCC19433 |
| 3 | Enterococcus faecalis | ATCC23655 |
| 4 | Lactobacillus rhamnosus | ATCC53103 |
| 5 | Lactobacillus acidophilus | JCM1132 |
| 6 | Lactobacillus casei | JCM1134 |
| 7 | Lactobacillus plantarum | JCM1149 |
| 8 | Lactobacillus gasseri | JCM5344 |
| 9 | Enterococcus faecium | JCM8714 |
| 10 | Enterococcus faecium | JCM8727 |
| 11 | Enterococcus faecalis | EC-12 |

Note that the isolation and culturing of the spleen cells from each knockout mouse, measurement of the amount of IL-12 protein in the culture supernatant, and preparation of the lactic acid bacteria added to each spleen cell were carried out as described below.

<Knockout Mice>

In this test example, 10-week-old, C57BL/6 strain mice deficient in TLR2 TLR4, TLR7, or Myd88 and a wild-type mouse were used. Note that as the wild-type mouse, a mouse purchased from Japan SLC, Inc. was used. Moreover, the TLR2-, TLR4-, TLR7-, or Myd88-deficient mice used were mice propagated in an SPF animal facility (in the absence of a specific pathogenic microbe) from mice obtained from Oriental BioService, Inc. Further, all of these mice were grown and fed constantly with rodents diet (product name: Labo MR Stock, manufactured by Nosan Corporation) and water. Furthermore, the experiment using these mice was conducted in accordance with the guidelines of the Committee for Animal Research of Kyoto Prefectural University for studies using experimental animals.

<Preparation of Spleen Cells>

A mouse was anesthetized by intraperitoneally injecting 30 µl of sodium pentobarbital (manufactured by Schering-Plough Corporation) and then bled. After the abdomen of the mouse was cut open, the spleen was extracted and immersed in an ice-cooled Hank's balanced salt solution. Subsequently, from the extracted spleen, spleen cells were isolated using a 70-µm cell strainer (manufactured by BD Falcon). Further, an ACK lysis solution (0.15 M $NH_4Cl$, 10 mM $KHCO_3$, and 0.1 mM $Na_2EDTA$, pH 7.4) was added to the isolated spleen cells, and the red blood cells were lysed. The spleen cells thus treated were washed twice with sterilized phosphate buffered saline, and suspended in a cell culture medium (RPMI 1640 supplemented with 10% fetal bovine serum (manufactured by Equitech-Bio), 100 U/ml penicillin, and 100 µg/ml streptomycin). Note that for the analysis, spleen cells isolated from three mice having the same genetic background were pooled and used. Moreover, as the control, spleen cells were similarly prepared from the wild-type mouse other than the above-described knockout mice.

<Culturing of Spleen Cells>

The number of living cells was counted by the trypan blue dye exclusion method. The spleen cells prepared as described above were seeded into each well of 96-well culture plate (manufactured by Orange Scientific) by $1 \times 10^6$ per well (100 µl of the cell culture medium). Then, 20 µg (wet weight) of viable bacteria or heat-killed bacteria suspended in 100 µl of a cell culture medium were added into each well, and the spleen cells and the lactic acid bacteria were co-cultured for 20 hours in a humid 5% $CO_2$ incubator. Note that the lactic acid bacterium and the spleen cells were co-cultured in a triplicate well.

<Quantification of IL-12p70>

After the culturing, the culture supernatant was collected. The concentration of the IL-12 protein in the culture supernatant was measured using mouse IL-12p70 DuoSet® ELISA Development System (manufactured by R&D Systems) in accordance with the instruction.

<Preparation of Lactic Acid Bacteria for Addition>

Five strains of *Lactobacillus* (*Lactobacillus acidophilus* strain JCM1132, *Lactobacillus casei* strain JCM1134, *Lactobacillus gasseri* strain JCM5344, *Lactobacillus plantarum* strain JCM1149 and *Lactobacillus rhamnosus* strain ATCC53103) and five strains of *Enterococcus* (*Enterococcus faecium* strain JCM8714, *Enterococcus faecium* strain JCM8727, *Enterococcus faecalis* strain ATCC14508, *Enterococcus faecalis* strain ATCC19433 and *Enterococcus faecalis* strain ATCC23655) were obtained from ATCC (American Type Culture Collection) or JCM (the Japan Collection of Microorganisms, Microbe Division, RIKEN BioResource Center). Moreover, *E. faecalis* strain EC-12 owned by Combi Corporation was used. Then, these lactic acid bacteria were cultured using lactobacilli MRS broth (manufactured by Difco) at 37° C. for hours. Thereafter, the bacteria were washed with sterilized water, and then centrifuged at 9000 g for 10 minutes to thereby collect bacterial cells. These were used as viable bacteria. Further, the bacterial cells were treated in a thermo alumi bath (manufactured by Iwaki) at 95° C. for 30 minutes, and thereby prepared as heat-killed bacteria.

Figure 8:
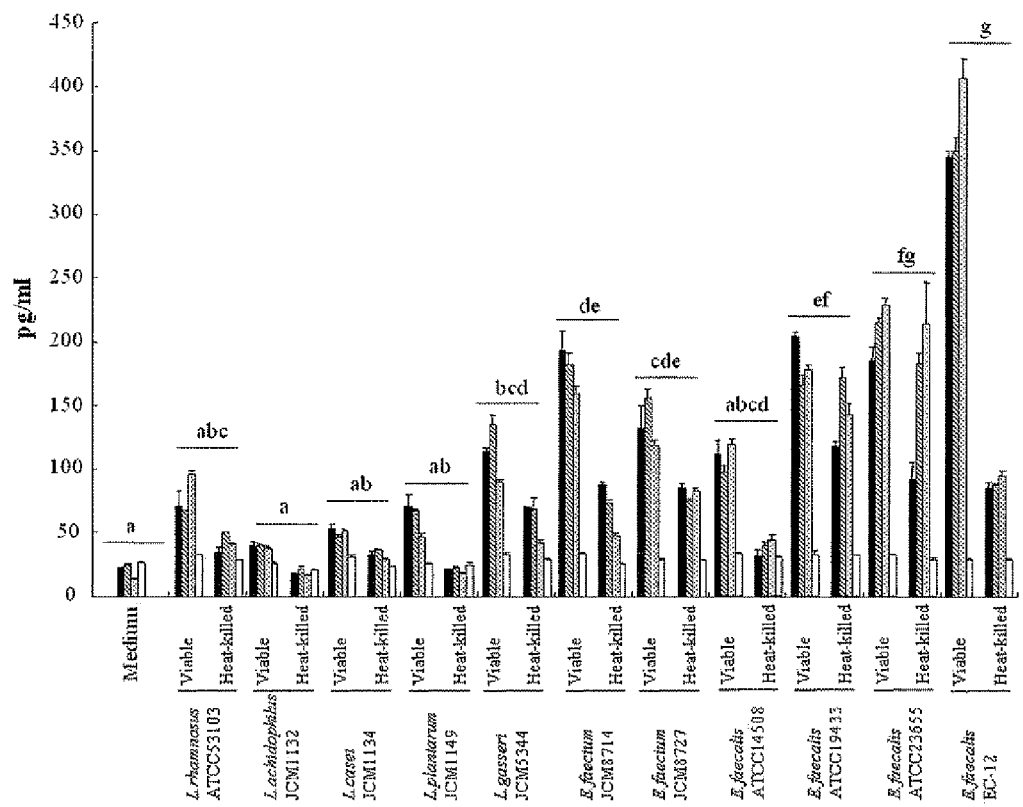
FIG. 8 shows bar graphs summarizing an ability to induce IL-12 production of bacterial cells of each lactic acid bacterium in Myd88, TLR2, or TLR4 knockout mice.
Figure 9:
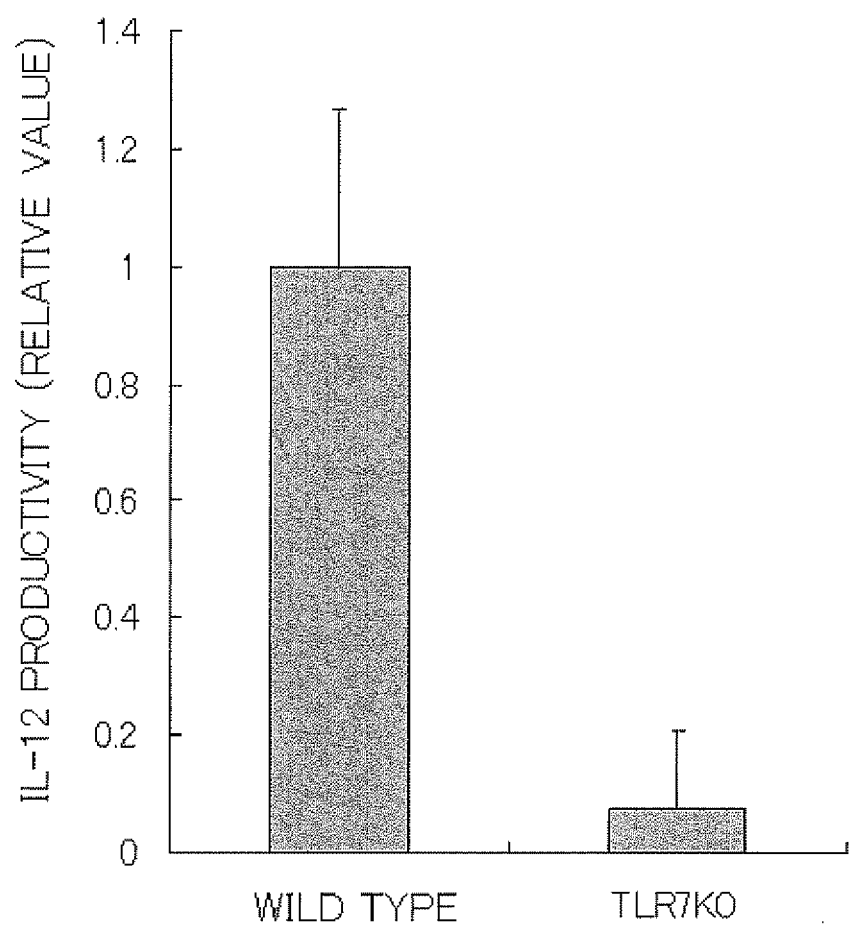
FIG. 9 shows a bar graph summarizing an ability to induce IL-12 production of EC-12 in a TLR7-knockout mouse.

FIG. 8 shows the result of the analysis conducted as described above on the Myd88-, TLR2-, or TLR4-knockout mice. In addition, FIG. 9 shows the result of the analysis conducted on the TLR7-knockout mouse. Note that, in FIG. 8, bar graphs indicated by "Viable" show the result of the co-culturing of the spleen cells derived from each knockout mouse with the viable bacteria; and bar graphs indicated by "Heat-Killed" show the result of the co-culturing with the heat-killed bacteria. Moreover, in FIG. 8, the black bar graphs show the result of the wild-type mouse; the white bar graphs show the result of the Myd88-knockout mouse; the hatched bar graphs show the result of TLR2-knockout mouse; and the dotted bar graphs show the result of the TLR4-knockout mouse (there were significant differences among the same signs (a to g: $p<0.05$).

As apparent from the result shown in FIG. 8, the spleen cells other than those from the Myd88-knockout mouse produced approximately the same amount of IL-12p70 as that from the wild-type mouse, while the IL-12p70 production was hardly observed from the spleen cells derived from the Myd88-knockout mouse. Moreover, such a trend was similarly recognized in both cases of the co-culturing with the viable bacteria and the co-culturing with the heat-killed bacteria.

Furthermore, as apparent from the result shown in FIG. 9, the amount of IL-12p70 produced by the spleen cells derived from the TLR7-knockout mouse was suppressed by 92.5% in comparison with that of the wild-type mouse. Thus, it was revealed that the lactic acid bacteria including EC-12 induced the IL-12 production independently of TLR2 and TLR4 but dependently on TLR7 or Myd88.

Example 2

Figure 10:
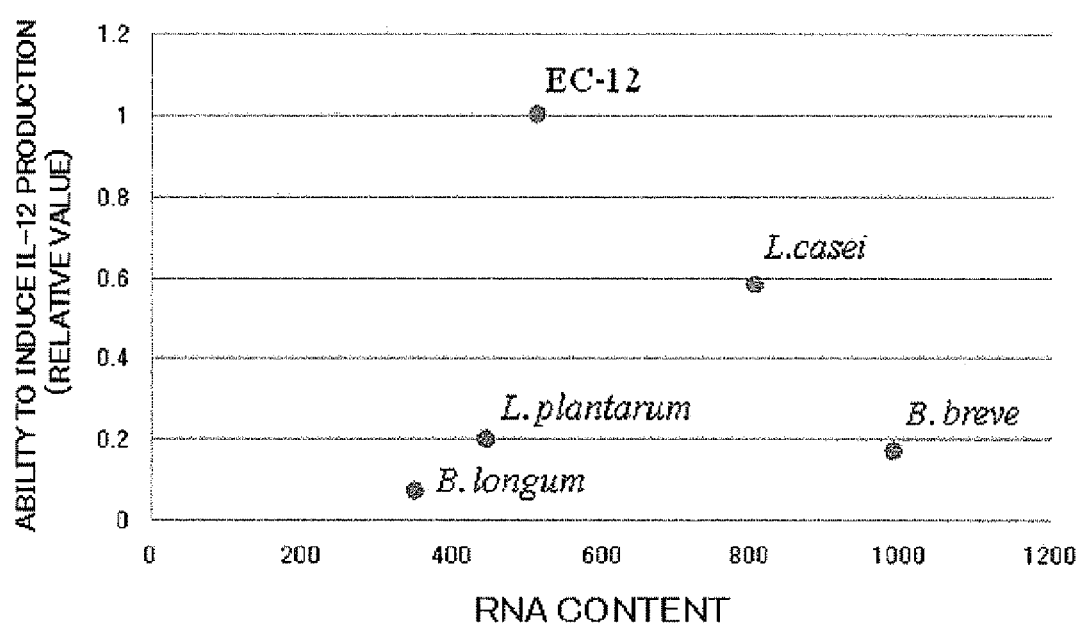
FIG. 10 shows a scatter graph illustrating a correlation between an RNA content of bacterial cells of each lactic acid bacterium and an ability to induce IL-12 production.
Figure 11:
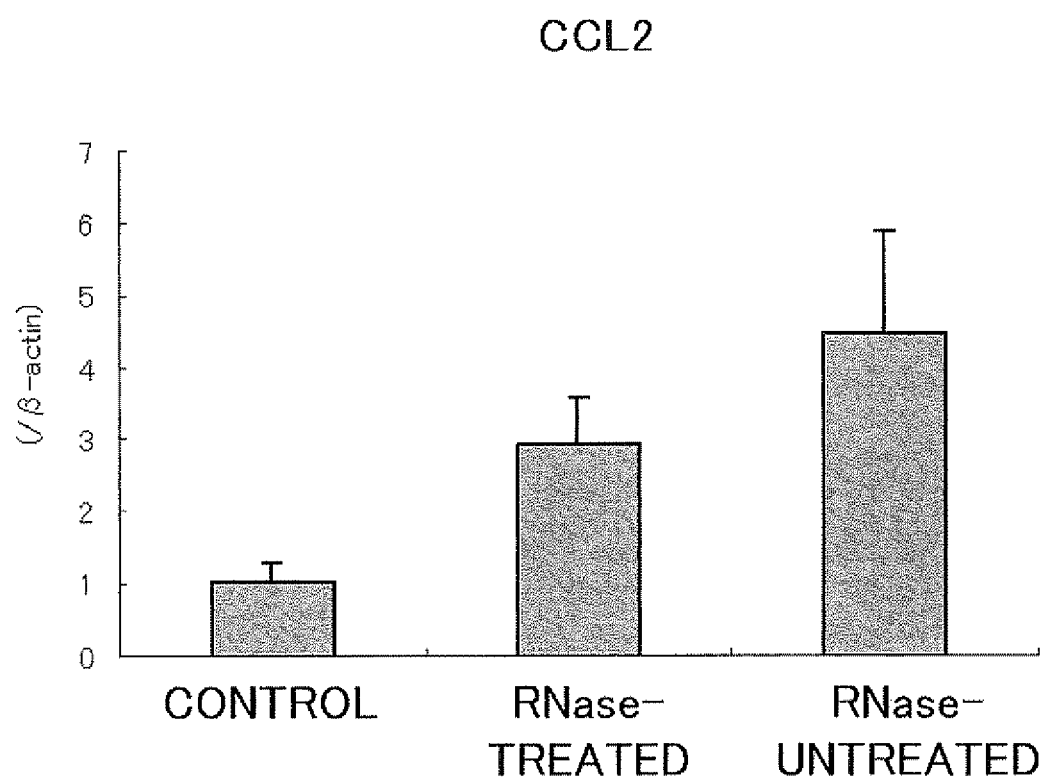
FIG. 11 shows a bar graph summarizing an ability to induce CCL2 production of an RNA derived from EC-12.
Figure 12:
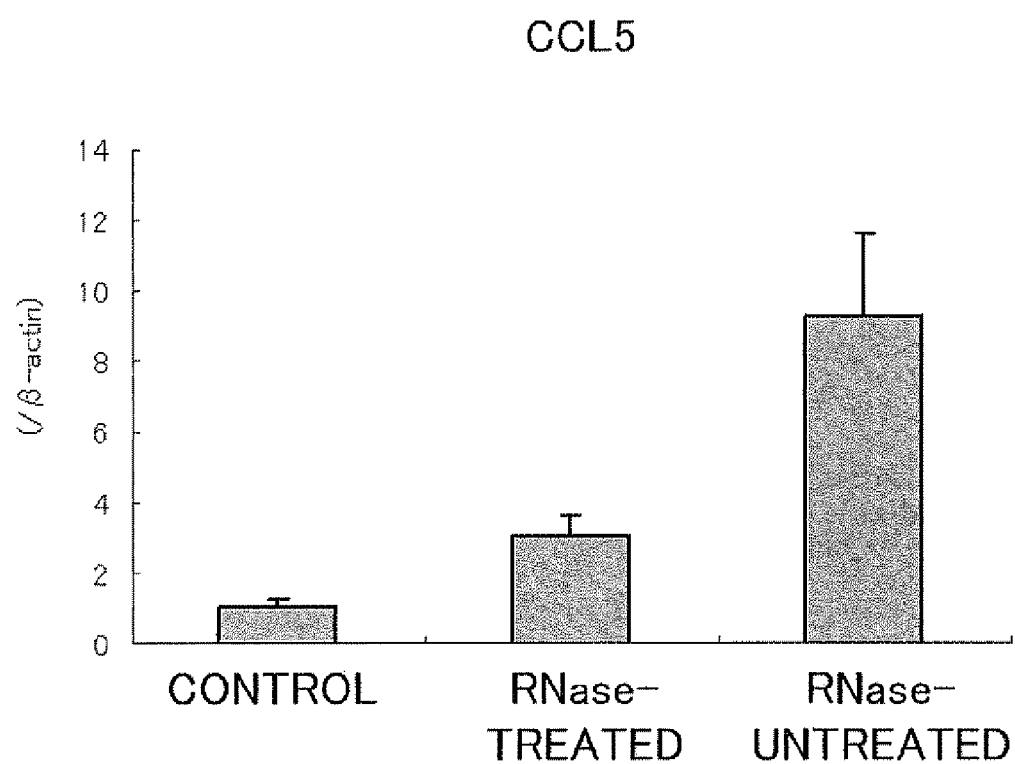
FIG. 12 shows a bar graph summarizing an ability to induce CCL5 production of an RNA derived from EC-12.
Figure 13:
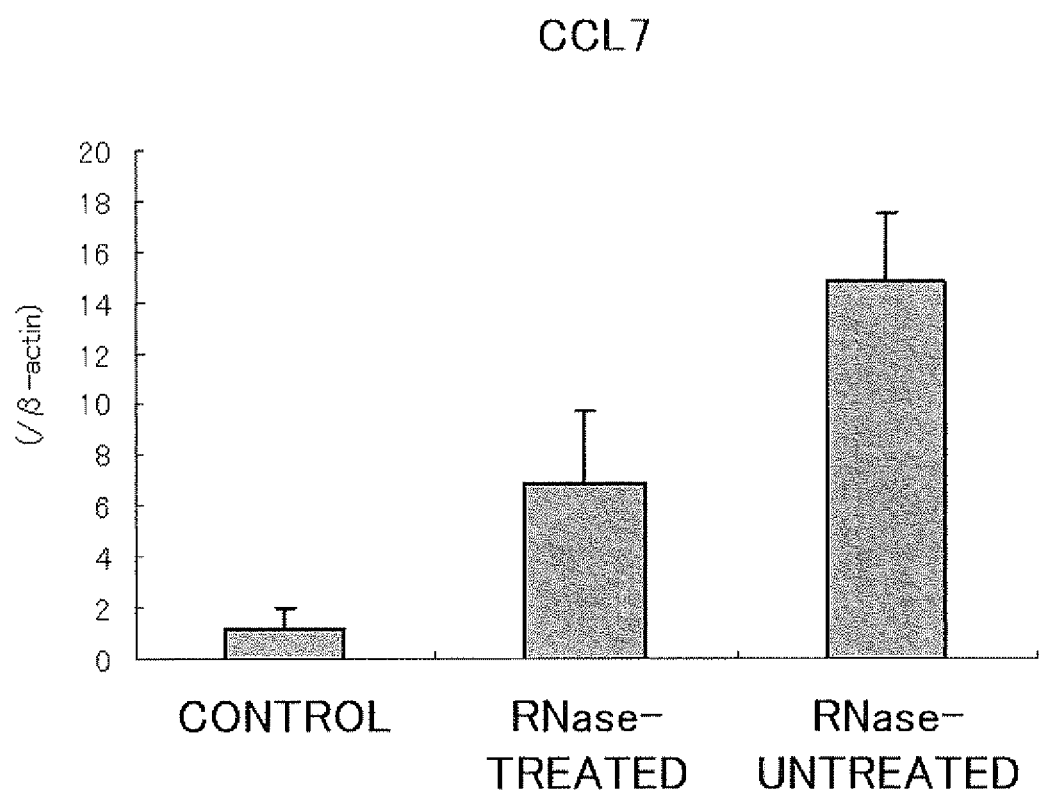
FIG. 13 shows a bar graph summarizing an ability to induce CCL7 production of an RNA derived from EC-12.
Figure 14:
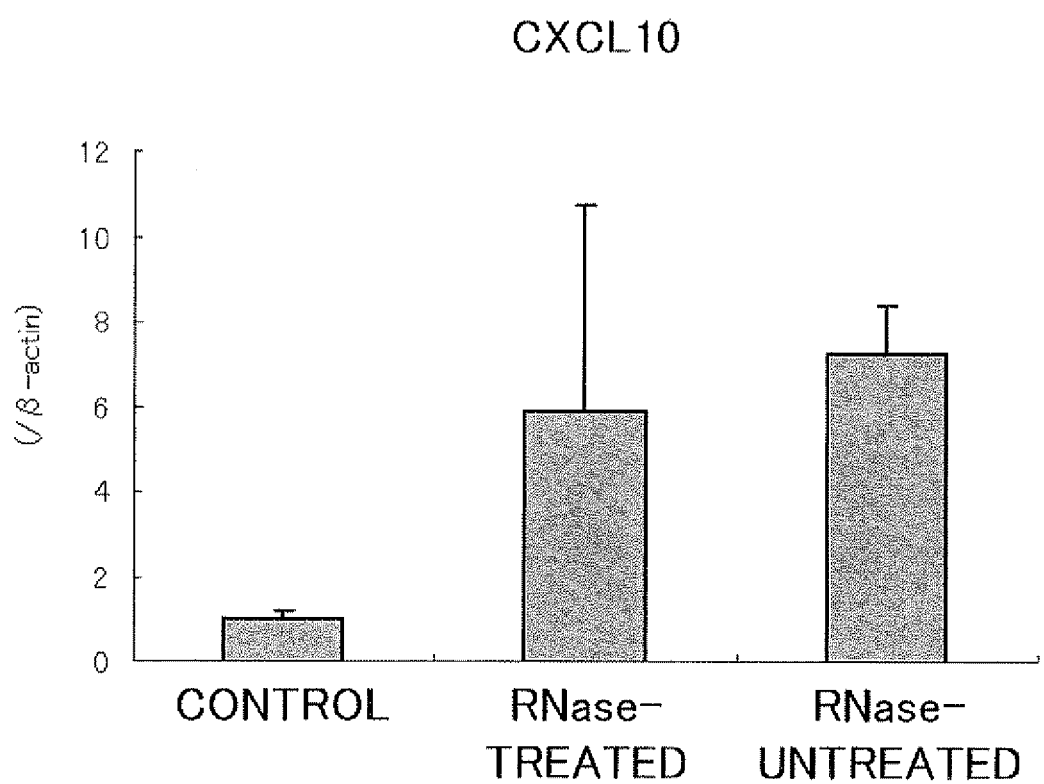
FIG. 14 shows a bar graph summarizing an ability to induce CXCL10 production of an RNA derived from EC-12.
Figure 15:
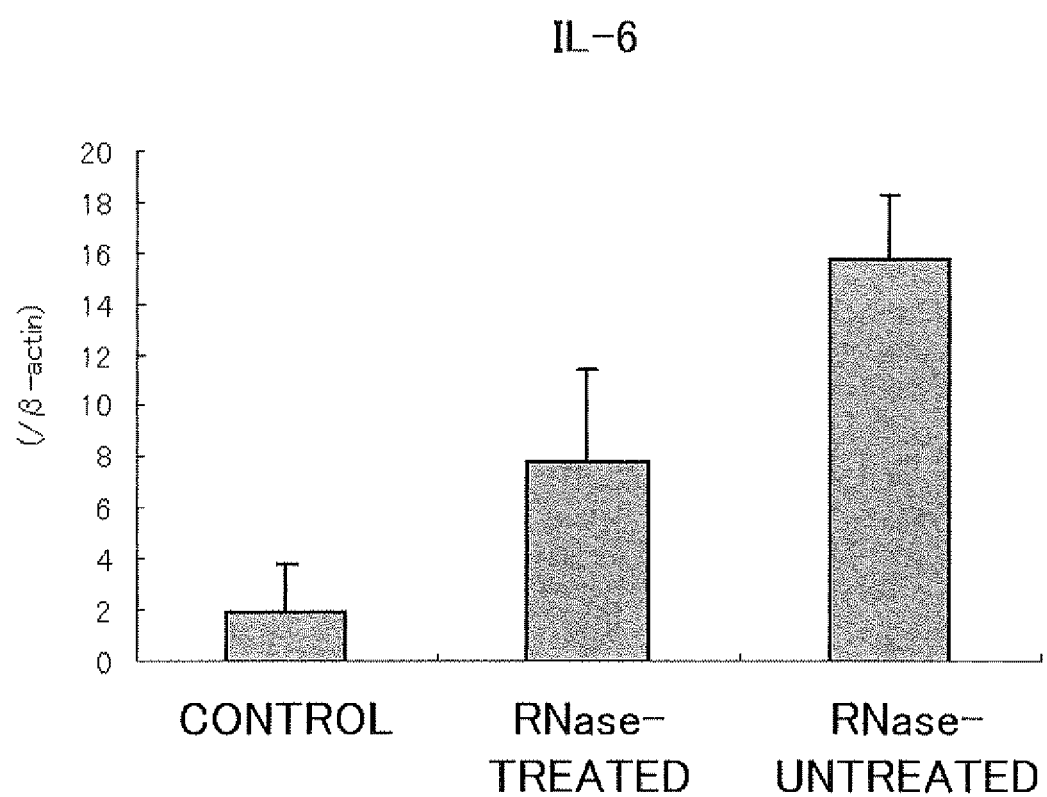
FIG. 15 shows a bar graph summarizing an ability to induce IL-6 production of an RNA derived from EC-12.
Figure 16:
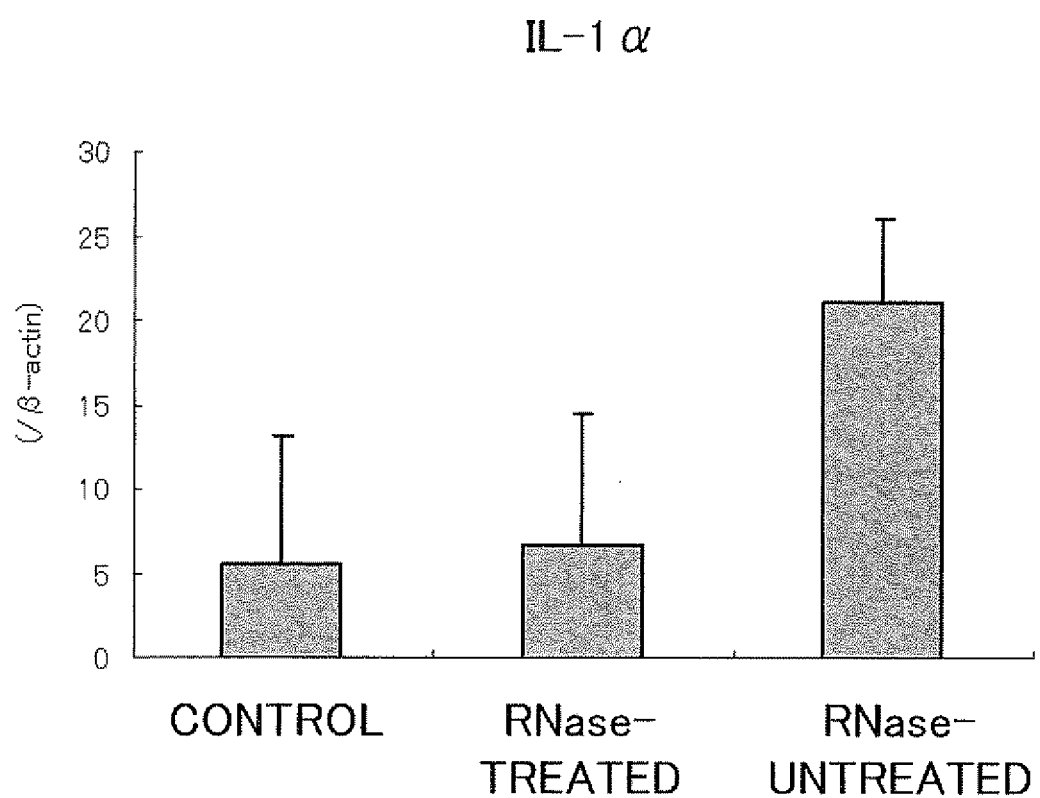
FIG. 16 shows a bar graph summarizing an ability to induce IL-1α production of an RNA derived from EC-12.
Figure 17:
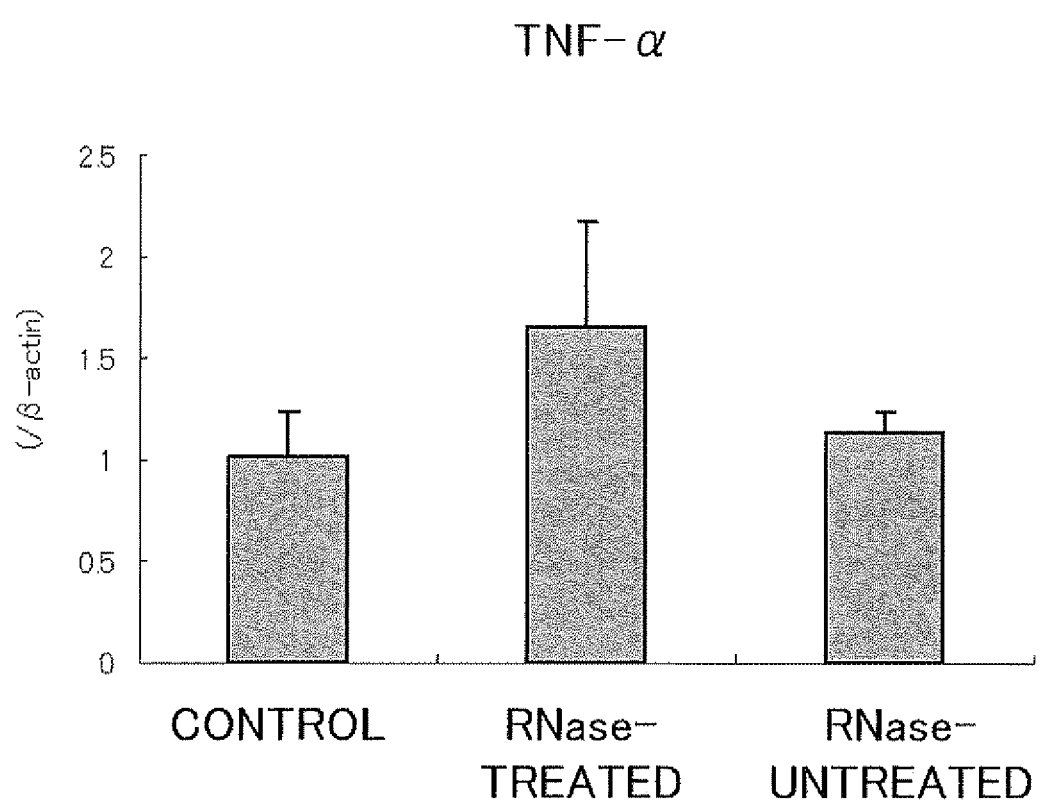
FIG. 17 shows a bar graph summarizing an ability to induce TNF-α production of an RNA derived from EC-12.

Examination on Ability to Induce IL-12 Production Attributable to RNA Content Next, the possibility that the IL-12 production was attributable to the RNA content of a bacterial strain was verified. Specifically, 150 mg of cells of each bacterium shown in Table 4 was treated in the same manner as in Test Example 4, and the amount of total RNA thus extracted was calculated based on the value of the absorbance at a wavelength of 260 nm measured using an absorption spectrometer (product name: NanoDrop, manufactured by LMS Co., Ltd.). Moreover, each total RNA thus obtained was introduced into a cell by the lipofection method in the same manner as in Example 1, and an IL-12p70 protein amount was measured in the same manner as in Test Example 6. FIG. 10 shows the obtained result.

TABLE 4

| Bacterium | Total RNA (ng/ml) |
| --- | --- |
| EC-12 | 513.4 |
| *Lactobacillus casei* | 803.3 |
| *Lactobacillus plantarum* | 447.4 |

TABLE 4-continued

| Bacterium | Total RNA (ng/ml) |
|---|---|
| Bifidobacterium breve | 988.9 |
| Bifidobacterium longum | 351.2 |

As apparent from the result shown in FIG. 10, although the RNA content was varied depending on the bacterial strain, a correlation between the RNA content and the IL-12 production was not observed. Thereby, the possibility that the difference in the IL-12 production among the bacterial strains was not simply attributable to the RNA content of the bacterial strain was found out to be high.

Example 3

Examination on Ability to Induce Cytokine•Chemokine Production Other Than IL-12 Attributable to RNA Derived from EC-12

Next, the influence of an RNA derived from EC-12 on expression of cytokine•chemokine other than IL-12 was examined. Specifically, first, total RNA derived from EC-12 and an RNase-treated product thereof were prepared in the same manner as in Example 1, and introduced into J774.1 cells by the lipofection method, followed by culturing. Next, an RNA was extracted from the cultured cells in the same manner as in Test Example 1. Using cytokine•chemokine array by real-time PCR, 15 genes except for IL-12 were selected whose amounts of expression would be possibly changed by the presence or absence of the RNA derived from EC-12. Specifically, the followings were conducted.

<Comprehensive Analysis Method for Amount of Genes such as Cytokine Expressed>

First, by a real-time PCR method using LIGHTCYCLER® 480, how much a housekeeping gene (glyceraldehyde-3-phosphate dehydrogenase: GAPDH) contained in each sample was expressed was determined. Then, in addition to Gapdh, Hipoxantine-guanine phosphoribosyltransferase (Hprt) and β-actin were also measured and used as housekeeping genes for correct ion when necessary. Designing of primers and selection of probes to be used were conducted on the website of Roche Applied Science. Moreover, the reaction using these primers was conducted using Taqman probe selected from LIGHTCYCLER® 480 PROBEMASTER (Roche Applied Science) and Universal Probe Library (manufactured by Roche Applied Science). Specifically, the reaction system was prepared by addition of 5 μl of PROBE-MASTER, 0.2 μl of each of forward and reverse primer solutions (10 pM), 0.1 μl of Universal Probe (10 pM) solution, 2.5 μl of sterile distilled water, and 2 μl of a template cDNA: 10 μl in total. Then, after the initial denaturing at 95° C. for 5 minutes, a temperature cycle consisting of 95° C. for 10 seconds and 60° C. for 20 seconds was repeated 50 times on the reaction system, and amplification curves were obtained. After the amplification was complete, the resultant was cooled at 40° C. for 30 seconds. Based on the Ct value obtained with LIGHTCYCLER 480® software (manufactured by Roche Applied Science), each cDNA solution was diluted with sterile distilled water in such a manner that the GAPDH genes were expressed in equal amounts.

Then, each group of the cDNA solutions thus prepared was pooled in a certain amount, and the amount of the genes such as cytokine expressed was comprehensively analyzed. Specifically, using primer sets shown in Tables 5 to 9, the real-time PCR method was carried out in the same manner as in the above-described measurement of the amount of the housekeeping gene expressed, and the amount of the genes such as cytokine expressed in each sample was measured.

TABLE 5

| Gene name | Forward | (SEQ ID NO) | Reverse | (SEQ ID NO) | Probe No. | Gene bank Accession No. |
|---|---|---|---|---|---|---|
| CC chemokine ligand | | | | | | |
| ccl1 | ccctgaagtttatccagtgtta | 8 | gcagctttctctacctttgttca | 9 | #63 | NM_011329 |
| ccl1[a] | gaagaaagagcttcccctgaa | 10 | cgcagctttctctacctttgtt | 11 | #47 | NM_011329 |
| ccl2 | catccacgtgttggctca | 12 | gatcatcttgctggtgaatgagt | 13 | #62 | NM_011333 |
| ccl3 | tgcccttgctgttcttctct | 14 | gtggaatcttccggctgtag | 15 | #40 | NM_011337 |
| ccl4 | gccctctatctcctcttgct | 16 | gagggtcagagcccattg | 17 | #1 | NM_013652 |
| ccl5 | tgcagaggactctgagacagc | 18 | gagtggtgtccgagccata | 19 | #110 | NM_013653 |
| ccl6 | ccttgtggctgtccttgg | 20 | gcgacgatcttcttttcca | 21 | #64 | NM_009139 |
| ccl7 | ttctgtgcctgctgctcata | 22 | ttgacatagcagcatgtggat | 23 | #89 | NM_013654 |
| ccl8 | ttctttgcctgctgctcata | 24 | gcaggtgactggagccttat | 25 | #26 | NM_021443 |
| ccl9 | tgggcccagatcacacat | 26 | cccatgtgaaacatttcaatttc | 27 | #98 | NM_011338 |
| ccl11 | cacggtcacttccttcacct | 28 | tggggatcttcttactggtca | 29 | #4 | NM_011330 |
| ccl12 | ccatcagtcctcaggtattgg | 30 | cttccggacgtgaatcttct | 31 | #93 | NM_011331 |
| ccl17 | tgcttctggggacttttctg | 32 | gaatggcccctttgaagtaa | 33 | #27 | NM_011332 |
| ccl19 | tgtggcctgcctcagattat | 34 | agtcttccgcatcattagcac | 35 | #40 | NM_011888 |
| ccl20 | aactgggtgaaaagggctgt | 36 | gtccaattccatcccaaaaa | 37 | #73 | NM_016960 |
| ccl21 | tccaagggctgcaagaga | 38 | tgaagttcgtgggggatct | 39 | #1 | NM_023052 |

TABLE 5-continued

| Gene name | Forward | (SEQ ID NO) | Reverse | (SEQ ID NO) | Probe No. | Gene bank Accession No. |
|---|---|---|---|---|---|---|
| ccl22 | tcttgctgtggcaattcaga | 40 | gagggtgacggatgtagtcc | 41 | #84 | NM_009137 |
| ccl24 | gcagcatctgtcccaagg | 42 | gcagcttggggtcagtaca | 43 | #9 | NM_019577 |
| ccl25 | gagtgccaccctaggtcatc | 44 | ccagctggtgcttactctga | 45 | #9 | NM_009138 |
| ccl26 | gcaccagtgacggtgtgata | 46 | tgaatctctgcacccatttg | 47 | #20 | NM_001013412 |
| ccl26[a] | cagtgtccagcttggtgttg | 48 | tgaaattagggcagcaggac | 49 | #32 | NM_001013412 |
| ccl27 | acagccactcccaegcag | 50 | aggtgacagtccccatcg | 51 | #101 | NM_011336 |
| ccl28 | gttcttcatcctgtggtgctc | 52 | agggaagactccacattcca | 53 | #38 | NM_020279 |

TABLE 6

| Gene name | Forward | (SEQ ID NO) | Reverse | (SEQ ID NO) | Probe No. | Gene bank Accession No. |
|---|---|---|---|---|---|---|
| CXC chemokine ligand | | | | | | |
| cxcl1 | ataatgggcttttacattctttaacc | 54 | agtcctttgaacgtctctgtcc | 55 | #2 | NM_008176 |
| cxcl2 | aaaatcatccaaaagatactgaacaa | 56 | ctttggttcttccgttgagg | 57 | #26 | NM_009140 |
| cxcl3 | ccccaggcttcagataatca | 58 | tctgatttagaatgcaggtcctt | 59 | #69 | NM_203320 |
| cxcl4 | tgggatccatcttaagcaca | 60 | ccattcttcagggtggctat | 61 | #64 | NM_019932 |
| cxcl5 | gggtgtgttaagagtgttcttacg | 62 | acacagcagctttctaaaaccat | 63 | #26 | NM_009141 |
| cxcl7 | gcccacttcataacctccag | 64 | atgggtccatgccatcag | 65 | #3 | NM_023785 |
| cxcl9 | cttttcctcttgggcatcat | 66 | gcatcgtgcattccttatca | 67 | #1 | NM_008599 |
| cxcl10 | gctgccgtcattttctgc | 68 | tctcactggcccgtcatc | 69 | #3 | NM_021274 |
| cxcl11 | gctgctgagatgaacaggaa | 70 | ccctgtttgaacataaggaagc | 71 | #76 | NM_019494 |
| cxcl12 | ctgtgcccttcagattgttg | 72 | taatttcgggtcaatgcaca | 73 | #41 | NM_021704 |
| cxcl13 | catagatcggattcaagttacgc | 74 | cacacatataactttcttcatcttggt | 75 | #46 | NM_018866 |
| cxcl14 | ttgagaccgttcacagcact | 76 | ctctctgagcggaagcctttg | 77 | #1 | NM_019568 |
| cxcl15 | tgctcaaggctggtccat | 78 | gacatcgtagctcttgagtgtca | 79 | #18 | NM_011339 |
| cxcl16 | tgaactagtggactgctttgagc | 80 | gcaaatgtttttggtggtga | 81 | #103 | NM_023158 |
| xcl1 | gacttctcctcctgactttcctg | 82 | ggacttcagtccccacacc | 83 | #74 | NM_008510 |
| cx3cl1 | cgcgttcttccatttgtgta | 84 | catgatttcgcatttcgtca | 85 | #74 | NM_009142 |

TABLE 7

| Gene name | Forward | (SEQ ID NO) | Reverse | (SEQ ID NO) | Probe No. | Gene bank Accession No. |
|---|---|---|---|---|---|---|
| Chemokine receptor | | | | | | |
| ccr1 | tggacaaaatactctaaaacaca | 86 | tgtgaaatctgaaatctccatcc | 87 | #73 | NM_009912 |
| ccr2 | acctgtaaatgccatgcaagt | 88 | tgtcttccattccttttgatttg | 89 | #27 | NM_009915 |
| ccr3 | gagcatcaacaacacgttcc | 90 | tgaaagtgtgatcttgggaca | 91 | #77 | NM_009914 |

TABLE 7-continued

| Gene name | Forward | (SEQ ID NO) | Reverse | (SEQ ID NO) | Probe No. | Gene bank Accession No. |
|---|---|---|---|---|---|---|
| ccr4 | ctcaggatcactttcagaagagc | 92 | ggcattcatctttggaatcg | 93 | #18 | NM_009916 |
| ccr5 | gagacatccgttcccctac | 94 | gtcggaactgacccttgaaa | 95 | #106 | NM_009917 |
| ccr6 | tggttcgccactctaatcagt | 96 | tctggtgtagaaagggaagtgg | 97 | #5 | NM_009835 |
| ccr7 | cagggaaacccaggaaaaac | 98 | atcttggcagaagcacacct | 99 | #77 | NM_007719 |
| ccr8 | agaagaaaggctcgctcaga | 100 | ggctccatcgtgtaatccat | 101 | #4 | NM_007720 |
| ccr9 | tctggcacagaagctgattg | 102 | catgccaggaataaggcttg | 103 | #105 | NM_009913 |
| ccr10 | accaacccacagagcag | 104 | gccaccatcagggagaca | 105 | #97 | NM_007721 |
| cxcr1 | ttctgagcttgctggggaaac | 106 | gggtccttcgcctgtataaga | 107 | #9 | NM_178241 |
| cxcr2 | caggaatgggagtaggtgga | 108 | tttcctagtttcccctccaaat | 109 | #32 | NM_009909 |
| cxcr3 | aggcagcacgagacctga | 110 | ggcatctagcacttgacgttc | 111 | #66 | NM_009910 |
| cxcr4 | tggaaccgatcagtgtgagt | 112 | gggcaggaagatcctattga | 113 | #38 | NM_009911 |
| cxcr5 | tttctgctcccagcatcc | 114 | ttttatttctgtgcccggttt | 115 | #103 | NM_007551 |
| cxcr6 | agctactgggcttctcttctga | 116 | tcgtagtgcccatcgtacag | 117 | #105 | NM_030712 |
| xcr1 | acatgataccatggggaagt | 118 | gtgcacgaagtgttgctttg | 119 | #11 | NM_011798 |
| cx3cr1 | aagttcccttcccatctgct | 120 | caaaattctctagatccagttcagg | 121 | #10 | NM_009987 |

TABLE 8

| Gene name | Forward | (SEQ ID NO) | Reverse | (SEQ ID NO) | Probe No. | Gene bank Accession No. |
|---|---|---|---|---|---|---|
| TLR and various chemokines | | | | | | |
| tlr1 | tcttgctggcacccattc | 122 | catgagagttttgagcttgtgg | 123 | #58 | NM_030682 |
| tlr2 | ggggcttcacttctctgctt | 124 | agcatcctctgagatttgacg | 125 | #50 | NM_011905 |
| tlr3 | gatacagggattgcacccata | 126 | tcccccaaaggagtacattaga | 127 | #26 | NM_126166 |
| tlr4 | ggactctgatcatggcactg | 128 | ctgatccatgcattggtaggt | 129 | #2 | NM_021297 |
| tlr5 | ctggagccgagtgaggtc | 130 | cggcaagcattgttctcc | 131 | #1 | NM_016928 |
| tlr5[a)] | tcatggatggatgctgagtt | 132 | tggccatgaagatcacacc | 133 | #18 | NM_016928 |
| tlr6 | ggtaccgtcagtgctggaa | 134 | gggttttctgtcttggctca | 135 | #110 | NM_011604 |
| tlr7 | gatcctggcctatctctgactc | 136 | cgtgtccacatcgaaaacac | 137 | #25 | NM_133211 |
| tlr8 | caaacgttttaccttcctttgtct | 138 | atggaagatggcactggttc | 139 | #56 | NM_133212 |
| tlr9 | gaatcctccatctcccaacat | 140 | ccagagtctcagccagcact | 141 | #79 | NM_031178 |
| Ifn-α | tcaagccatccttgtgctaa | 142 | gtcttttgatgtgaagaggttcaa | 143 | #3 | NM_010504 |
| Ifn-β | ctggcttccatcatgaacaa | 144 | agagggctgtggtggagaa | 145 | #18 | NM_010510 |
| Ifn-β[a)] | cacagccctctccatcaacta | 146 | catttccgaatgttcgtcct | 147 | #78 | NM_010510 |
| Ifn-γ | atctggaggaactggcaaaa | 148 | ttcaagacttcaaagagtctgagg | 149 | #21 | NM_008337 |
| tnf-α | tcttctcattcctgcttgtgg | 150 | ggtctgggccatagaactga | 151 | #49 | NM_013693 |
| tgf-β1 | tggagcaacatgtggaactc | 152 | cagcagccggttaccaag | 153 | #72 | NM_011577 |
| Il-1α | ttggttaaatgacctgaca | 154 | gagcgctcacgaacagttg | 155 | #52 | NM_010554 |
| Il-1β | tgtaatgaaagacggcacacc | 156 | tcttctttgggtattgcttgg | 157 | #78 | NM_008361 |

TABLE 8-continued

| Gene name | Forward | (SEQ ID NO) | Reverse | (SEQ ID NO) | Probe No. | Gene bank Accession No. |
|---|---|---|---|---|---|---|
| Il-2 | gctgttgatggacctacagga | 158 | ttcaattctgtggcctgctt | 159 | #15 | NM_008366 |
| Il-3 | tacatctgcgaatgactctgc | 160 | ggctgaggtggtctagaggtt | 161 | #94 | NM_010556 |
| Il-4 | gagagatcatcggcattttga | 162 | tctgtggtgttcttcgttgc | 163 | #2 | NM_021283 |
| Il-5 | acattgaccgccaaaagag | 164 | atccaggaactgcctcgtc | 165 | #91 | NM_010558 |
| Il-6 | gatggatgctaccaaactgga | 166 | ccaggtagctatggtactccagaa | 167 | #6 | NM_031168 |
| Il-7 | cgcagaccatgttccatgt | 168 | tctttaatgtggcactcagatgat | 169 | #27 | NM_008371 |

15

TABLE 9

| Gene name | Forward | (SEQ ID NO) | Reverse | (SEQ ID NO) | Probe No. | Gene bank Accession No. |
|---|---|---|---|---|---|---|
| Various chemokines, adhesion factor, costimulator, housekeeping gene, etc | | | | | | |
| Il-10 | cagagccacatgctcctaga | 170 | tgtccagctggtcctttgtt | 171 | #41 | NM_010548 |
| Il-13 | cctctgaccccttaaggagcttat | 172 | cgttgcacaggggagtct | 173 | #27 | NM_008352 |
| Il-17a | tgtgaaggtcaacctcaaagtc | 174 | agggatatctatcagggtcttcatt | 175 | #50 | NM_008355 |
| Il-18 | catgtacaaagacagtgaagtaagagg | 176 | tttcaggtggatccatttcc | 177 | #74 | NM_010552 |
| aprll | ggtggtatctcgggaaggac | 178 | cccccttgatgtaaatgaaagaca | 179 | #7 | NM_008360 |
| baff | aacagacacgctttccag | 180 | aggaggagctgagaggtctacat | 181 | #6 | NM_023517 |
| cd80 | ttcgtctttcacaagtgtcttca | 182 | tgccagtagattcggtcttca | 183 | #91 | NM_033622 |
| cd86 | gaagccgaatcagcctagc | 184 | cagcgttactatcccgctct | 185 | #107 | NM_009855 |
| tslf | cagcttgtctcctgaaaatcg | 186 | aaatgttttgtcggggagtg | 187 | #71 | NM_019388 |
| slpl | cttgctctggggatcctg | 188 | ggctccgatttgatagcat | 189 | #12 | NM_021367 |
| nod2 | tgtggagtcaccgcaaaac | 190 | tcctctgtgcctggaactct | 191 | #100 | NM_011414 |
| α4 integrin | caaaccagacctgcgaaca | 192 | tgtcttcccacaaggctctc | 193 | #45 | NM_145857 |
| β7 integrin | ctgctgcctctccatctgta | 194 | aaaaatgagaacagttgatgaatcc | 195 | #63 | NM_010576 |
| madcam-1 | gggcaggtgaccaatctgta | 196 | ataggacgacggtggagga | 197 | #72 | NM_013566 |
| hprt | tcctcctcagaccgctttt | 198 | cctggttcatcatcgctaatc | 199 | #95 | NM_013591 |
| β-actin | ctaaggccaaccgtgaaaag | 200 | accagaggcatacagggaca | 201 | #64 | NM_013556 |
| gapdh | tgtccgtcgtggatctgac | 3 | cctgcttcaccaccttcttg | 4 | #80 | NM_007393 |
| plgR | agtaaccgaggcctatcctt | 202 | gtcactcggcaactcagga | 203 | #64 | NM_008084 |
| Il-12p40 | gactccaggggacaggcta | 204 | ggagatggttagcttctgagga | 205 | #27 | NM_008352 |

Figure 18:
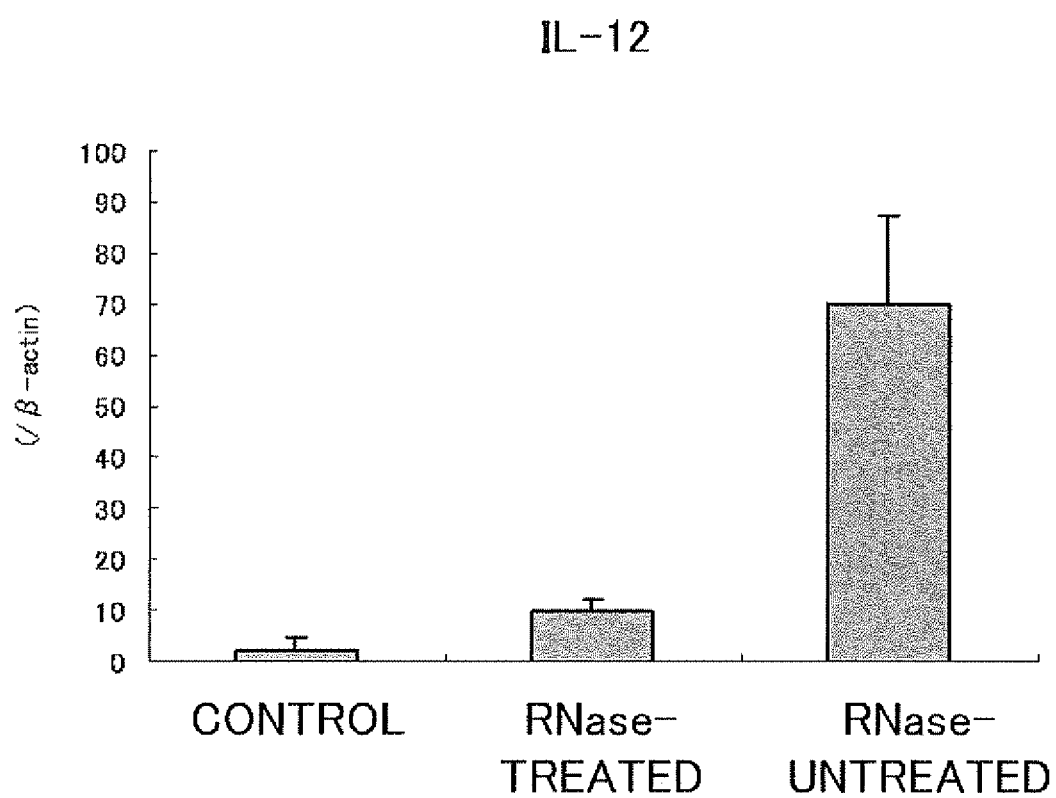
FIG. 18 shows a bar graph summarizing an ability to induce IL-12 production of an RNA derived from EC-12.

Further, individual analyses (real-time PCR) were conducted on 15 genes except for IL-12, which were selected by such a comprehensive analysis. Genes whose amounts of expression were significantly changed by whether the RNase treatment was conducted or not were further selected. FIGS. 11 to 17 show the obtained results. Moreover, FIG. 18 shows the result of IL-12. Note that, in FIGS. 11 to 18, the vertical axis indicates the amount of each gene expressed normalized by the amount of β-actin expressed, and bar graphs indicated by "control" show the result of the cells cultured with no additive.

As apparent from the results shown in FIGS. 11 to 18, the RNase treatment significantly changed the expressions of the genes CCL2, CCL5, CCL7, CXCL10, IL-6, IL-1α, and TNF-α, and the RNase treatment lowered the expressions of the genes other than TNF-α. However, since these decreased amounts were small relative to that of the IL-12 gene, this suggested that IL-12 was a cytokine the most strongly influenced by the RNase treatment. Meanwhile, the RNase treatment increased the amount of TNF-α expressed. In other words, it was revealed that introduction of an RNA derived from a lactic acid bacterium into a cell promoted production of IL-12, CCL2, CCL5, CCL7, CXCL10, IL-6, and IL-1α, but suppressed production of TNF-α.

INDUSTRIAL APPLICABILITY

As described hereinabove, according to the present invention, by activating signaling and the like dependently on TLR7 and Myd88 in a living organism, an RNA derived from a lactic acid bacterium comprised as an effective component can promote production of IL-12 and the like, or suppress production of TNF-α Moreover, according to the present invention, a reduction in the immune function in the living organism is suppressed by stimulating the immune function, and an excessive enhancement of the immune function is suppressed without adversely influencing the living organism. Thus, the balance of the immune function can be adjusted. Furthermore, lactic acid bacteria have been contained in fermentation foods such as fermented milks from the past, and the dietary practice is long. Hence, the lactic acid bacterium according to the present invention is considered to be highly safe.

Accordingly, the composition of the present invention is excellent in safely suppressing a reduction in the immune function by stimulating the immune function. Therefore, the composition of the present invention is useful as a composition for oral intake, and the like for targeting intestinal function regulation, cancer risk reduction, prevention of atopic dermatitis, allergy reduction, infection defense, and so on.

The invention claimed is:

1. A composition for modulating a cytokine production, comprising:
   a single-stranded RNA derived from a lactic acid bacterium as an effective component; and
   a positively charged carrier for introducing the single-stranded RNA into a cell;
   wherein the lactic acid bacterium is at least one lactic acid bacterium selected from the group consisting of lactic acid bacteria belonging to genera *Enterococcus, Lactobacillus, Lactococcus, Streptococcus, Pediococcus*, and *Leuconostoc*.

2. The composition according to claim 1, wherein the composition promotes production of at least one cytokine selected from the group consisting of Interleukin-12 (IL-12), Chemokine (C-C motif) ligand 2 (CCL2), Chemokine (C-C motif) ligand 5 (CCL5), Chemokine (C-C motif) ligand 7 (CCL7), Chemokine (C-X-C motif) ligand 10 (CXCL10), Interleukin-6 (IL-6), and Interleukin-1 alpha (IL-1α).

3. The composition according to claim 2, wherein the Interleukin-12 (IL-12) is Interleukin-12p40 (IL-12p40).

4. The composition according to claim 1, wherein the composition suppresses production of Tumor necrosis factor-alpha (TNF-α).

5. The composition according to claim 1, wherein the composition modulates the cytokine production dependently on at least one biomolecule selected from the group consisting of Toll-like receptor 7 (TLR7) and Myeloid differentiation primary response gene 88 (Myd88).

6. The composition according to claim 1, wherein the lactic acid bacterium is *Enterococcus faecalis*.

7. The composition according to claim 1, wherein the lactic acid bacterium is *Enterococcus faecalis* EC-12.

8. The composition according to claim 1, wherein the composition is a composition for oral intake.

9. A method for modulating a cytokine production, comprising introducing into a cell the composition according to claim 1.

* * * * *